United States Patent
Yamamura et al.

(10) Patent No.: US 10,828,303 B2
(45) Date of Patent: Nov. 10, 2020

(54) COMPOSITION COMPRISING COMBINATION OF TRH ANALOG WITH ARUNDIC ACID, AND PHARMACEUTICALLY ACCEPTABLE SALT OF ARUNDIC ACID

(71) Applicant: Brivention Pharmaceutical (Shanghai) Inc., Shanghai (CN)

(72) Inventors: Michio Yamamura, Tokyo (JP); Narito Tateishi, Tokyo (JP)

(73) Assignee: BRIVENTION PHARMACEUTICAL (SHANGHAI) INC., Shanghai (CN)

( * ) Notice: Subject to any disclaimer, the term of this patent is extended or adjusted under 35 U.S.C. 154(b) by 0 days.

(21) Appl. No.: 16/338,594

(22) PCT Filed: Sep. 27, 2017

(86) PCT No.: PCT/JP2017/034926
§ 371 (c)(1),
(2) Date: Apr. 1, 2019

(87) PCT Pub. No.: WO2018/066427
PCT Pub. Date: Apr. 12, 2018

(65) Prior Publication Data
US 2019/0240221 A1    Aug. 8, 2019

(30) Foreign Application Priority Data

Oct. 3, 2016 (JP) .................. 2016-195505
Sep. 26, 2017 (JP) .................. 2017-184731

(51) Int. Cl.
| | |
|---|---|
| *C07C 53/128* | (2006.01) |
| *A61K 31/513* | (2006.01) |
| *A61P 25/28* | (2006.01) |
| *A61P 9/10* | (2006.01) |
| *A61P 25/10* | (2006.01) |
| *A61K 31/20* | (2006.01) |
| *A61P 43/00* | (2006.01) |
| *A61P 21/02* | (2006.01) |
| *A61P 25/16* | (2006.01) |

(52) U.S. Cl.
CPC ............ *A61K 31/513* (2013.01); *A61K 31/20* (2013.01); *A61P 9/10* (2018.01); *A61P 21/02* (2018.01); *A61P 25/10* (2018.01); *A61P 25/16* (2018.01); *A61P 25/28* (2018.01); *A61P 43/00* (2018.01); *C07C 53/128* (2013.01)

(58) Field of Classification Search
CPC ..................................................... A61K 31/513
See application file for complete search history.

(56) References Cited

U.S. PATENT DOCUMENTS

| | | | |
|---|---|---|---|
| 6,201,021 B1 | 3/2001 | Ohuchida et al. | |
| 7,176,240 B2 | 2/2007 | Ohuchida et al. | |
| 7,569,608 B2 | 8/2009 | Ohuchida et al. | |
| 7,569,609 B2 | 8/2009 | Ohuchida et al. | |
| 7,820,715 B2 | 10/2010 | Hasegawa et al. | |
| 8,273,916 B2 | 9/2012 | Hasegawa et al. | |
| 2003/0096802 A1 | 5/2003 | Ohuchida et al. | |
| 2005/0261371 A1 | 11/2005 | Ohuchida et al. | |
| 2005/0267167 A1 | 12/2005 | Ohuchida et al. | |
| 2005/0267168 A1 | 12/2005 | Ohuchida et al. | |
| 2008/0090907 A1* | 4/2008 | Hasegawa ............ C07C 53/128 514/557 |
| 2010/0226943 A1* | 9/2010 | Brennan ................ A61L 2/02 424/400 |
| 2010/0331414 A1 | 12/2010 | Hasegawa et al. | |

FOREIGN PATENT DOCUMENTS

| | | |
|---|---|---|
| JP | 62-234029 A | 10/1987 |
| JP | H07-082166 A | 3/1995 |
| JP | H07-316092 A | 12/1995 |
| JP | 2006-143708 A | 6/2006 |
| WO | 2005/105722 A1 | 11/2005 |

OTHER PUBLICATIONS

Wippagunta et al. (2001).*
Wolff et al. (1997).*
Banker et al. (1995).*
Kwon et al., "List of Drugs in Development for Neurodegenerative Diseases", Neurodegenerative Dis, 2004, vol. 1, pp. 113-152.
Yamamura et al., "Pharmacological Study of TA-0910, a New Thyrotropin-Releasing Hormone (TRH) Analog (IV): Effects on Experimental Memory Impairment in Mice and Rats", Japan J. Pharmacol., 1991, vol. 55, pp. 241-253.
Pulsinelli et al., "A New Model of Bilateral Hemispheric Ischemia in the Unanesthetized Rat", Stroke, 1979, vol. 10, No. 3, pp. 267-272.
Johansen et al., "Resistance of Hippocampal CA-1 Interneurons to 20 min of Transient Cerebral Ischemia in the Rat", Acta Neuropathol., 1983, vol. 61, No. 2, pp. 135-140.

* cited by examiner

*Primary Examiner* — Paul V Ward
(74) *Attorney, Agent, or Firm* — MH2 Technology Law Group, LLP

(57) ABSTRACT

An object of this invention is to provide a composition for preventing and/or treating neurodegenerative diseases and cerebral infarction, and a composition for ameliorating learning disorders.
Provided is a composition comprising a combination of a TRH analog and arundic acid.

10 Claims, 42 Drawing Sheets

Fig. 28-2

Peak Search Report (3 Peaks, Max P/N = 10.6)
PEAK: 27-pts/Parabolic Filter, Threshold=3.0, Cutoff=0.1%, BG=3/1.0, Peak-Top=Summit

| No. | 2-Theta | d(A) | BG | Height | Heighest I% | Area | Area I% | FWHM |
|---|---|---|---|---|---|---|---|---|
| 1 | 5.445 | 16.2176 | 558 | 735 | 100 | 17396 | 91.1 | 0.397 |
| 2 | 5.959 | 14.8191 | 436 | 719 | 97.8 | 19094 | 100 | 0.445 |
| 3 | 6.352 | 13.9031 | 272 | 522 | 71 | 11927 | 62.5 | 0.383 | d(A) = d spacing(A),BG = back ground signal,Height = peak height
I% = percentage compared with the highest area,FWHM = full width at half maximum

Fig. 29-2

Peak Search Report (3 Peaks, Max P/N = 11.3)

PEAK: 27-pts/Parabolic Filter, Threshold=3.0, Cutoff=0.1%, BG=3/1.0, Peak-Top=Summit

| No. | 2-Theta | d(A) | BG | Height | Height I% | Area | Area I% | FWHM |
|---|---|---|---|---|---|---|---|---|
| 1 | 5.328 | 16.5727 | 489 | 812 | 100 | 16788 | 100 | 0.347 |
| 2 | 5.86 | 15.0692 | 421 | 744 | 91.6 | 15419 | 91.8 | 0.347 |
| 3 | 6.353 | 13.9007 | 252 | 515 | 63.4 | 10110 | 60.2 | 0.329 | d(A) = d spacing(A), BG = back ground signal, Height = peak height.
I% = percentage compared with the highest area, FWHM = full width at half maximum

Fig. 30-2

Peak Search Report (15 Peaks, Max P/N = 16.9)

PEAK: 17-pts/Parabolic Filter. Threshold=3.0, Cutoff=0.1%, BG=3/1.0, Peak-Top=Summit

| No. | 2-Theta | d(A) | BG | Height | Heighest I% | Area | Area I% | FWHM |
|---|---|---|---|---|---|---|---|---|
| 1 | 5.034 | 17.5394 | 442 | 1479 | 100 | 11728 | 100 | 0.133 |
| 2 | 5.819 | 15.1766 | 383 | 1146 | 77.5 | 9887 | 84.3 | 0.145 |
| 3 | 6.373 | 13.8566 | 353 | 528 | 35.7 | 4690 | 40 | 0.149 |
| 4 | 6.592 | 13.3973 | 320 | 500 | 33.8 | 3420 | 29.2 | 0.115 |
| 5 | 7.41 | 11.9201 | 233 | 108 | 7.3 | 1324 | 11.3 | 0.206 |
| 6 | 7.594 | 11.6318 | 226 | 76 | 5.1 | 1557 | 13.3 | 0.343 |
| 7 | 8.316 | 10.6239 | 196 | 50 | 3.4 | 353 | 3 | 0.118 |
| 8 | 9.173 | 9.6333 | 175 | 78 | 5.3 | 1170 | 10 | 0.251 |
| 9 | 9.511 | 9.2909 | 175 | 64 | 4.3 | 776 | 6.6 | 0.203 |
| 10 | 10.098 | 8.7524 | 165 | 69 | 4.7 | 527 | 4.5 | 0.126 |
| 11 | 11.594 | 7.6263 | 152 | 62 | 4.2 | 767 | 6.5 | 0.207 |
| 12 | 17.853 | 4.9643 | 142 | 54 | 3.7 | 1025 | 8.7 | 0.318 |
| 13 | 18.63 | 4.7587 | 155 | 46 | 3.1 | 383 | 3.3 | 0.14 |
| 14 | 19.127 | 4.6363 | 160 | 91 | 6.2 | 698 | 6 | 0.129 |
| 15 | 19.804 | 4.4793 | 168 | 50 | 3.4 | 580 | 4.9 | 0.194 | d(A) = d spacing(A), BG = back ground signal, Height = peak height
I% = percentage compared with the highest area, FWHM = full width at half maximum

Fig. 31-2

Peak Search Report (7 Peaks, Max P/N = 14.4)

PEAK: 21-pts/Parabolic Filter, Threshold=3.0, Cutoff=0.1%, BG=3/1.0, Peak-Top=Summit

| No. | 2-Theta | d(A) | BG | Height | Heighest I% | Area | Area I% | FWHM |
|---|---|---|---|---|---|---|---|---|
| 1 | 5.054 | 17.4719 | 557 | 484 | 39.5 | 4713 | 23.9 | 0.163 |
| 2 | 5.327 | 16.5758 | 544 | 1127 | 92 | 19714 | 100 | 0.293 |
| 3 | 5.877 | 15.0247 | 577 | 1225 | 100 | 13170 | 66.8 | 0.18 |
| 4 | 6.371 | 13.8608 | 271 | 809 | 66 | 13210 | 67 | 0.274 |
| 5 | 9.628 | 9.1782 | 183 | 60 | 4.9 | 346 | 1.8 | 0.097 |
| 6 | 10.727 | 8.2409 | 172 | 64 | 5.2 | 1422 | 7.2 | 0.373 |
| 7 | 29.391 | 3.0364 | 77 | 51 | 4.2 | 568 | 2.9 | 0.187 | d(A) = d spacing(A),BG = back ground signal,Height = peak height
I% = percentage compared with the highest area,FWHM = full width at half maximum

Fig. 32-2

Peak Search Report (24 Peaks, Max P/N = 17.6)
PEAK: 19-pts/Parabolic Filter, Threshold=3.0, Cutoff=0.1%, BG=3/1.0, Peak-Top=Summit

| No. | 2-Theta | d(A) | BG | Height | Heighest I% | Area | Area I% | FWHM |
|---|---|---|---|---|---|---|---|---|
| 1 | 5.071 | 17.4103 | 399 | 1559 | 100 | 14540 | 100 | 0.156 |
| 2 | 5.862 | 15.0644 | 352 | 1230 | 78.9 | 12046 | 82.8 | 0.164 |
| 3 | 6.416 | 13.7645 | 319 | 627 | 40.2 | 6953 | 47.8 | 0.186 |
| 4 | 6.649 | 13.2818 | 290 | 636 | 40.8 | 6182 | 42.5 | 0.163 |
| 5 | 7.471 | 11.8225 | 223 | 147 | 9.4 | 2117 | 14.6 | 0.241 |
| 6 | 8.419 | 10.4938 | 197 | 59 | 3.8 | 665 | 4.6 | 0.189 |
| 7 | 9.216 | 9.5884 | 184 | 118 | 7.6 | 950 | 6.5 | 0.135 |
| 8 | 9.608 | 9.1973 | 176 | 84 | 5.4 | 456 | 3.1 | 0.091 |
| 9 | 10.157 | 8.702 | 169 | 88 | 5.6 | 698 | 4.8 | 0.133 |
| 10 | 10.514 | 8.4072 | 175 | 69 | 4.4 | 466 | 3.2 | 0.113 |
| 11 | 11.661 | 7.5823 | 161 | 61 | 3.9 | 605 | 4.2 | 0.166 |
| 12 | 12.717 | 6.9553 | 148 | 53 | 3.4 | 251 | 1.7 | 0.079 |
| 13 | 14.085 | 6.2825 | 146 | 60 | 3.8 | 578 | 4 | 0.162 |
| 14 | 14.779 | 5.9892 | 148 | 70 | 4.5 | 710 | 4.9 | 0.17 |
| 15 | 15.422 | 5.7407 | 161 | 60 | 3.8 | 636 | 4.4 | 0.178 |
| 16 | 15.996 | 5.5362 | 163 | 54 | 3.5 | 347 | 2.4 | 0.108 |
| 17 | 17.635 | 5.025 | 176 | 69 | 4.4 | 1918 | 13.2 | 0.466 |
| 18 | 17.889 | 4.9542 | 181 | 96 | 6.2 | 1636 | 11.3 | 0.286 |
| 19 | 18.684 | 4.7452 | 193 | 58 | 3.7 | 1108 | 7.6 | 0.32 |
| 20 | 19.167 | 4.6268 | 207 | 138 | 8.9 | 2861 | 19.7 | 0.348 |
| 21 | 19.631 | 4.5185 | 213 | 54 | 3.5 | 999 | 6.9 | 0.31 |
| 22 | 19.845 | 4.4701 | 220 | 98 | 6.3 | 1002 | 6.9 | 0.171 |
| 23 | 21.249 | 4.1779 | 216 | 51 | 3.3 | 855 | 5.9 | 0.281 |
| 24 | 22.47 | 3.9535 | 189 | 61 | 3.9 | 1832 | 12.6 | 0.504 | d(A) = d spacing(A),BG = back ground signal,Height = peak height
I% = percentage compared with the highest area,FWHM = full width at half maximum

Fig. 33-2

Peak Search Report (28 Peaks, Max P/N = 18.6)
PEAK: 17-pts/Parabolic Filter, Threshold=3.0, Cutoff=0.1%, BG=3/1.0, Peak-Top=Summit

| No. | 2-Theta | d(A) | BG | Height | Heighest I% | Area | Area I% | FWHM |
|---|---|---|---|---|---|---|---|---|
| 1 | 4.453 | 19.8277 | 442 | 83 | 4.7 | 440 | 3.3 | 0.089 |
| 2 | 5.072 | 17.4091 | 407 | 1749 | 100 | 13205 | 100 | 0.127 |
| 3 | 5.861 | 15.0675 | 368 | 1403 | 80.2 | 10396 | 78.7 | 0.124 |
| 4 | 6.43 | 13.7336 | 356 | 593 | 33.9 | 4518 | 34.2 | 0.128 |
| 5 | 6.634 | 13.313 | 328 | 546 | 31.2 | 2837 | 21.5 | 0.087 |
| 6 | 7.46 | 11.8408 | 229 | 127 | 7.3 | 1318 | 10 | 0.174 |
| 7 | 7.919 | 11.1558 | 213 | 33 | 1.9 | 151 | 1.1 | 0.072 |
| 8 | 8.33 | 10.6051 | 189 | 66 | 3.8 | 517 | 3.9 | 0.131 |
| 9 | 9.193 | 9.6117 | 168 | 85 | 4.9 | 1022 | 7.7 | 0.202 |
| 10 | 9.591 | 9.2141 | 159 | 83 | 4.7 | 810 | 6.1 | 0.164 |
| 11 | 10.144 | 8.7133 | 155 | 63 | 3.6 | 698 | 5.3 | 0.186 |
| 12 | 10.494 | 8.423 | 157 | 69 | 3.9 | 614 | 4.6 | 0.149 |
| 13 | 11.032 | 8.0133 | 155 | 31 | 1.8 | 421 | 3.2 | 0.214 |
| 14 | 11.655 | 7.5867 | 148 | 70 | 4 | 817 | 6.2 | 0.196 |
| 15 | 12.623 | 7.0067 | 133 | 54 | 3.1 | 418 | 3.2 | 0.13 |
| 16 | 12.799 | 6.911 | 138 | 42 | 2.4 | 374 | 2.8 | 0.149 |
| 17 | 13.287 | 6.6581 | 131 | 41 | 2.3 | 333 | 2.5 | 0.136 |
| 18 | 14.994 | 5.9038 | 130 | 45 | 2.6 | 424 | 3.2 | 0.158 |
| 19 | 15.336 | 5.7727 | 134 | 48 | 2.7 | 939 | 7.1 | 0.328 |
| 20 | 15.996 | 5.5359 | 136 | 48 | 2.7 | 658 | 5 | 0.23 |
| 21 | 17.889 | 4.9542 | 144 | 58 | 3.3 | 1633 | 12.4 | 0.472 |
| 22 | 18.665 | 4.75 | 151 | 58 | 3.3 | 734 | 5.6 | 0.212 |
| 23 | 19.096 | 4.6437 | 151 | 103 | 5.9 | 904 | 6.8 | 0.147 |
| 24 | 19.553 | 4.5361 | 155 | 45 | 2.6 | 706 | 5.3 | 0.263 |
| 25 | 19.856 | 4.4678 | 151 | 78 | 4.5 | 1712 | 13 | 0.368 |
| 26 | 20.501 | 4.3287 | 159 | 44 | 2.5 | 831 | 6.3 | 0.298 |
| 27 | 21.295 | 4.169 | 150 | 43 | 2.5 | 706 | 5.3 | 0.275 |
| 28 | 22.386 | 3.9682 | 138 | 46 | 2.6 | 582 | 4.4 | 0.2 | d(A) = d spacing(A), BG = back ground signal, Height = peak height
I% = percentage compared with the highest area, FWHM = full width at half maximum

COMPOSITION COMPRISING COMBINATION OF TRH ANALOG WITH ARUNDIC ACID, AND PHARMACEUTICALLY ACCEPTABLE SALT OF ARUNDIC ACID

CROSS-REFERENCE TO RELATED APPLICATIONS

This application is a U.S. National Stage application of PCT/JP2017/034926 filed 27 Sep. 2017, which claims priority to Japanese Application No. 2016-195505 filed 3 Oct. 2016 and Japanese Application No. 2017-184731 filed 26 Sep. 2017, the entire disclosures of which are incorporated herein by reference.

TECHNICAL FIELD

The present invention relates to a composition comprising a combination of a TRH analog and arundic acid. In particular, the present invention relates to a composition for use in the prevention and/or treatment of a neurodegenerative disease selected from dementia, Parkinson's disease, amyotrophic lateral sclerosis, Steele-Richardson-Olszewski syndrome, multiple system atrophy, and triplet repeat disease, or cerebral infarction; and a composition for use in ameliorating a learning disorder. The present invention also relates to a pharmaceutically acceptable salt of arundic acid.

BACKGROUND ART

According to the website of the Ministry of Health, Labour and Welfare, dementia is defined as a state in which one cannot lead his/her everyday life or social life as a result of a chronic decline in or loss of various kinds of psychic functions that developed once normally after birth. The website also states that the number of persons suffering from dementia has been increasing year by year since 1995, and that the number of elderly people population with dementia is 2.62 million (2015), indicating that its prevalence in the elderly population aged 65 years or older is 8.4%. Further, its prevalence in the elderly population aged 65 years or older is expected to become 8.9% in 2020.

Symptoms of dementia are manifested as behavioral disorders/psychiatric symptoms (e.g., Verbal abuse/violence, wandering/disappearance, and delusion), in addition to cognitive dysfunction of memory etc. (impairment of the ability to learn new information and/or recall previously learned information).

Administering thyrotropin-releasing hormone (TRH) to patients with Alzheimer's disease or patients with cerebrovascular dementia has recently been reported to improve the level of arousal, mood, semantic memory, etc. Additionally, TA-0910 (taltirelin), which is a TRH analog, has been reported to exhibit a higher improvement effect thereon than TRH, and has been reported to improve memory retrieval in an one-trial passive avoidance learning test by administering TA-0910 to rats with anoxia-induced amnesia. TA-0910 has also been reported to improve memory retrieval in an active avoidance learning test by administering TA-0910 to rats with lesioned bilateral regions including the ventral globus pallidus, substantia innominata, and preoptic area (BFs) (Non-patent Literature 1). Further, taltirelin is known to be used for the prevention and/or treatment of shock symptoms (Patent Literature 1).

The function of neurons, such as nutrition supply, waste excretion, and ion balance maintenance, is supported by glial cells such as astrocytes and Schwann cells. In addition to maintenance of the cell function of neurons, glial cells maintain the ability to metabolize glutamic acid and γ-aminobutyric acid, and the ability to produce neuropeptides and cytokines; and play an important role in controlling brain function. 2-propyloctanoic acid (arundic acid) is known as a function-improving agent for glial cells (Patent Literature 2). It has been reported that $GABA_A$ receptor responsiveness is recovered by allowing 2-propyloctanoic acid to act on reactive astrocytes (Patent Literature 2).

CITATION LIST

Patent Literature

PTL 1: JPH07-082166A
PTL 2: JPH07-316092A

Non-Patent Literature

NPL 1: Yamamura M, et al., 1991, Japan. J. Pharmacol. Vol. 55. p. 241-253

SUMMARY OF INVENTION

Technical Problem

The Ministry of Health, Labour and Welfare is also currently working on protection of elderly persons with dementia, such as providing a special website for unidentified elderly persons with dementia etc. as part of the Dementia Measure Promotion Comprehensive Strategy (New Orange Plan). Dementia is diagnosed based on DSM-IV of the American Psychiatric Association; however, patients who satisfy these diagnosis criteria are in far-advanced stages of dementia. It has thus been stated that such criteria do not lead to early treatment. Mild cognitive impairment (MCI) is a mild cognitive disorder that is a precursor to dementia including Alzheimer's disease. Treatment should begin at this stage, or at an earlier stage. However, for example, donepezil hydrochloride, which is an anticholinesterase inhibitor used as a therapeutic agent for Alzheimer's disease, is considered less effective in suppressing the progression of Alzheimer's disease.

In view of the state of the art described above, an object of the present invention is to provide a composition for preventing (including suppressing progression) and/or treating neurodegenerative diseases including dementia and cerebral infarction. Another object of the present invention is to provide a composition for suppressing progression of and/or treating neurodegenerative diseases including dementia; and learning disorders associated with ischemic brain disease, in particular, spatial cognitive impairment.

Still another object of the present invention is to provide a pharmaceutically acceptable salt of arundic acid, and a pharmaceutically acceptable solvate thereof.

Solution to Problem

The present inventors conducted extensive research, and found that administering a TRH analog and arundic acid in combination improves performance in a Morris water maze test in a four-vessel occlusion model of rats. That is, the inventors found that administering a TRH analog and arundic acid in combination ameliorates learning disorders. The present inventors obtained pharmaceutically acceptable salts of arundic acid, and pharmaceutically acceptable solvates thereof.

The present invention has been accomplished based on the above finding, and includes the following embodiments.

I. Composition

I-1. A composition comprising, combination,
(A) at least one member selected from the group consisting of compounds represented by Formula (I), pharmaceutically acceptable salts thereof, and hydrates thereof (hereinafter may be referred to as a "TRH analog" in the present specification) and (B) at least one member selected from the group consisting of arundic acid, pharmaceutically acceptable salts thereof, and pharmaceutically acceptable solvates thereof:

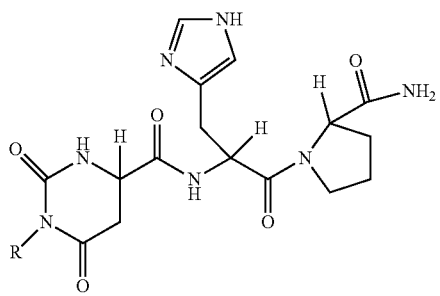

(I)

wherein R is hydrogen or $C_{1-6}$ alkyl.

I-2. The composition according to I-1, which is in a form of a combination preparation of component (A) and component (B) mixed beforehand.

I-3. The composition according to I-1, which is used in a form in which component (A) and component (B) are mixed at the time of use. This form includes a kit comprising at least a preparation containing component (A) and a preparation containing component (B).

I-4. The composition according to any one of I-1 to I-3, wherein component (A) is a hydrate of the compound represented by Formula (I).

I-5. The composition according to any one of I-1 to I-4, wherein R is methyl.

I-6. The composition according to any one of I-1 to I-5, wherein component (B) is arundic acid.

I-7. The composition according to any one of I-1 to I-5, wherein component (B) is an arundic acid salt represented by Formula (II) or a pharmaceutically acceptable solvate thereof:

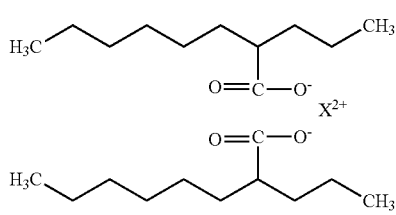

(II)

wherein $X^{2+}$ is a divalent cation.

I-8. The composition according to 1-7, wherein $X^{2+}$ is $Ca^{2+}$, $Mg^{2+}$, $Fe^{2+}$, $Ba^{2+}$, $^+H_3N-NH_3^+$, $^+H_2N=NH_2^+$, or $^+H\equiv NH^+$.

I-9. The composition according to any one of I-1 to I-8, which is a pharmaceutical composition.

I-10. The composition according to any one of I-1 to I-9, which is a composition for the prevention and/or treatment of a neurodegenerative disease selected from dementia, Parkinson's disease, amyotrophic lateral sclerosis, Steele-Richardson-Olszewski syndrome, multiple system atrophy, and triplet repeat disease; or cerebral infarction.

I-11. The composition according to any one of I-1 to I-8 and I-10, which is a food composition.

I-12. The composition according to any one of I-1 to I-11, which is for use in ameliorating a learning disorder.

I-13. The composition according to I-12, wherein the learning disorder is spatial cognitive impairment.

II. Arundic Acid Salt, Production Method Therefor, and Use of Arundic Acid Salt

II-1. A compound represented by Formula (II) or a solvate thereof:

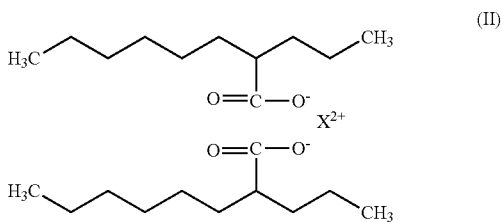

(II)

wherein $X^{2+}$ is a divalent cation.

II-2. The compound or a solvate thereof according to II-1, wherein $X^{2+}$ is $Ca^{2+}$, $Mg^{2+}$, $Fe^{2+}$, $Ba^{2+}$, $^+H_3N-NH_3^+$, $^+H_2N=NH_2^+$, or $^+H\equiv NH^+$.

II-3. The compound or a solvate thereof according to II-1, wherein $X^{2+}$ is $Ca^{2+}$, and the compound has a crystal structure.

II-4. The compound or a solvate thereof according to II-2, wherein the crystal is a crystal set forth in Table 1 or 2.

II-5. A method for producing a compound represented by Formula (II):

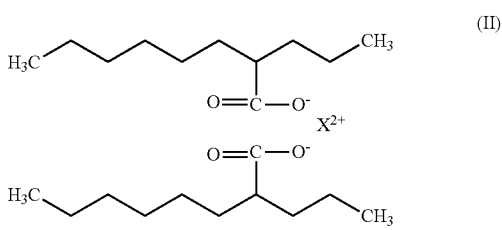

(II)

wherein $X^{2+}$ is a divalent cation,
the method comprising allowing a divalent cation to act on arundic acid in a solvent.

II-6. The method for producing a compound according to II-5, wherein $X^{2+}$ is $Ca^{2+}$, $Fe^{2+}$, $Ba^{2+}$, $^{+H}_3N-NH_3^+$, $^+H_2N=NH_2^+$, or $^+HN\equiv NH^+$.

II-7. The method according to II-5, wherein the solvent is at least one member selected from the group consisting of methyl tert-butyl ether, acetonitrile, and dichloromethane.

II-8. A composition comprising at least one member selected from the group consisting of the compound according to any one of II-1 to II-4, and pharmaceutically acceptable solvates thereof.

II-9. The composition according to II-8, wherein the composition is used in combination with a TRH analog, a pharmaceutically acceptable salt thereof, and a hydrate thereof.

II-10. The composition according to II-8 or II-9, wherein the composition is a pharmaceutical composition.

II-11. The composition according to any one of II-8 to II-10, which is for use in improving a function of astrocytes, or changing reactive astrocytes to astrocytes.

II-12. The composition according to any one of II-8 to II-10, which is for use in the treatment and/or prevention of a neurodegenerative disease, neurological dysfunction after brain and spinal cord traumatic injury, brain tumor, cerebrospinal disease associated with infection, or multiple sclerosis.

II-13. The composition according to II-12, wherein the neurodegenerative disease is dementia, amyotrophic lateral sclerosis, Steele-Richardson-Olszewski syndrome, or multiple system atrophy.

II-14. The composition according to II-12, wherein the cerebrospinal disease associated with infection is meningitis, brain abscess, Creutzfeldt-Jakob disease, or AIDS dementia.

II-15. The composition according to II-12, wherein the brain tumor is an astrocytoma.

II-16. The composition according to any one of II-8, II-9, and II-11 to II-14, wherein the composition is a food composition.

Advantageous Effects of Invention

Administering a TRH analog and arundic acid in combination enables spatial memory impairment to be ameliorated. Moreover, when a TRH analog and arundic acid are administered in combination, learning disorders can be ameliorated and neuronal cells shed due to ischemia can be regenerated, at doses less than those when the TRH analog or arundic acid is administered alone.

BRIEF DESCRIPTION OF DRAWINGS

FIG. 28-1 shows an XRPD spectrum of Compound of Synthesis Example 12.

FIG. 28-2 shows XRPD peak values of Compound of Synthesis Example 12.

FIG. 29-1 shows an XRPD spectrum of Batch No. 05.
FIG. 29-2 shows XRPD peak values of Batch No. 05.
FIG. 30-1 shows an XRPD spectrum of Batch No. 08.
FIG. 30-2 shows XRPD peak values of Batch No. 08.
FIG. 31-1 shows an XRPD spectrum of Batch No. 10.
FIG. 31-2 shows XRPD peak values of Batch No. 10.
FIG. 32-1 shows an XRPD spectrum of Batch No. 11.
FIG. 32-2 shows XRPD peak values of Batch No. 11.
FIG. 33-1 shows an XRPD spectrum of Batch No. 12.
FIG. 33-2 shows XRPD peak values of Batch No. 12.

DESCRIPTION OF EMBODIMENTS

I. Composition

Figure 1:
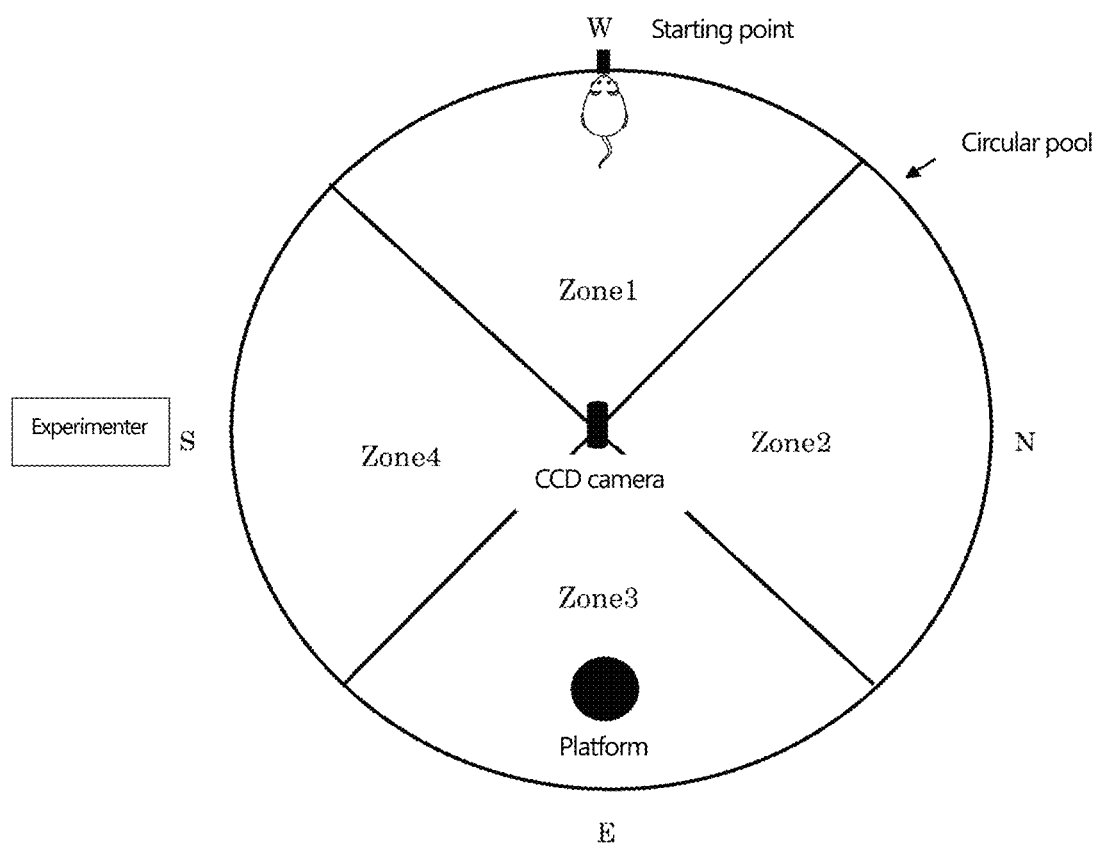
FIG. 1 is a plan view of a Morris water maze, and also shows a laboratory layout.

I-1. Components of Composition and Combination Composition

The composition of the present invention is a composition comprising, in combination, (A) at least one member selected from the group consisting of TRH analogs, pharmaceutically acceptable salts thereof, and hydrates thereof; and (B) at least one member selected from the group consisting of arundic acid, pharmaceutically acceptable salts thereof, and pharmaceutically acceptable solvates thereof, i.e., a combination composition.

The TRH analog as used herein refers to a compound represented by Formula (I):

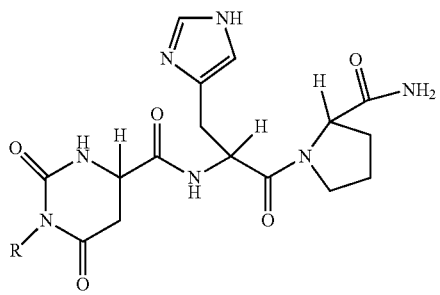

wherein R is hydrogen or $C_{1-6}$ alkyl, preferably $C_{1-4}$ alkyl.

R is preferably hydrogen, methyl, ethyl, propyl, isopropyl, butyl, isobutyl, sec-butyl, or tert-butyl; preferably hydrogen, methyl, or ethyl; and more preferably methyl.

The compound represented by Formula (I) is most preferably a compound represented by Formula (I-1); this is also referred to as taltirelin or N-[(4S)-1-methyl-2,6-dioxo-hexahydropyridine-4-carbonyl]-L-histidyl-L-prolinamide.

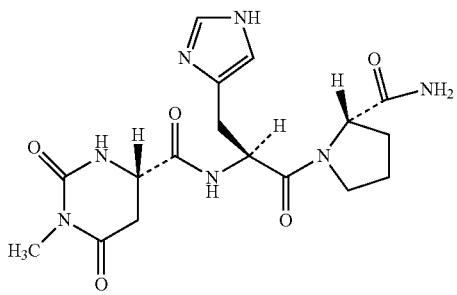

Examples of pharmaceutically acceptable salts of the compound represented by Formula (I) or Formula (I-1) include, but are not limited to, inorganic acid addition salts, such as hydrochloride, hydrobromide, sulfate, and nitrate; and organic acid addition salts, such as acetate, tartrate, maleate, succinate, citrate, methanesulfonate, malate, oxalate, and benzenesulfonate. These salts can be produced, for example, by treating the compound represented by Formula (I) with an acid.

Examples of solvents for forming the compound represented by Formula (I) or Formula (I-1), or a solvent that forms a pharmaceutically acceptable salt and solvate is not particularly limited. The solvent, for example, include, but are not limited to, water, ethanol, acetone, acetic acid, 1-propanol, 2-propanol, ethyl acetate, diethyl ether, and the like. The solvent is preferably water or ethanol, and more preferably water.

Arundic acid as used herein refers to a compound represented by the following formula.

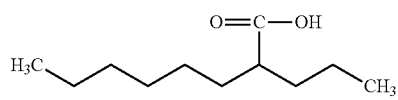

Arundic acid may be an R-form, S-form, or racemic form. Arundic acid is also referred to by its IUPAC name, 2-propyloctanoic acid.

Examples of solvents for forming arundic acid and solvates thereof include, but are not limited to, methanol, ethanol, acetone, ethyl acetate, chloroform, diethyl ether, and acetonitrile. The solvent is preferably ethanol, acetone, ethyl acetate, diethyl ether, or a mixture thereof.

Examples of pharmaceutically acceptable salts of arundic acid include, but are not limited to, sodium salt, potassium salt, and salts represented by Formula (II):

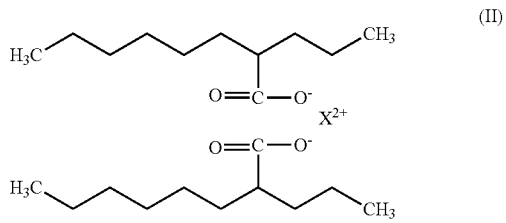

wherein $X^{2+}$ is a divalent cation.

The pharmaceutically acceptable salt of arundic acid is preferably a compound represented by Formula (II), in particular, preferably a compound in which $X^{2+}$ is $Ca^{2+}$, $Mg^{2+}$, $Fe^{2+}$, $Ba^{2+}$, $^+H_3N—NH_3^+$, $^+H_2N=NH_{2+}$, or $^+HN\equiv NH^+$; and more preferably a compound in which $X^{2+}$ is $Ca^{2+}$, among the compounds represented by Formula (II).

The pharmaceutically acceptable salt of arundic acid includes enantiomers, an amorphous form, and those in a crystalline form. In particular, when $X^{2+}$ is $Ca^{2+}$, the salt is preferably crystalline. Further, the crystals are preferably at least one selected from the group consisting of crystal 1 or 2 exhibiting the first to third peaks shown in Table 1 as representative peaks in X-ray powder diffraction (XRPD) under the following conditions, and crystals 3 to 5 exhibiting the first to fourth peaks shown in Table 2 as representative peaks in X-ray powder diffraction (XRPD) under the following conditions. Crystals 3 to 5 preferably have the first to seventh peaks shown in Table 2. It is particularly preferable that crystal 1 has the peaks shown in FIG. 28, that crystal 2 has the peaks shown in FIG. 29, that crystal 3 has the peaks shown in FIG. 30, that crystal 4 has the peaks shown in FIG. 31, and that crystal 5 has the peaks shown in FIG. 32. The value of 2θ(°) in the present specification and drawings may include errors of about ±0.2°, and preferably about ±0.1°. The full width at half-maximum (FWHM) in the present specification and drawings may include errors of about ±0.1°, and preferably about ±0.05°.

Analysis conditions

Tube: Cu K-alpha (λ=1.54179 Å)

Generator: Voltage: 40 kV; Current: 40 mA

Scan range: 3 to 40 deg.

Sample rotation speed: 15 rpm.

Scan speed: 10 deg./min

TABLE 1

|  |  | Crystal 1 | Crystal 2 |
|---|---|---|---|
| First peak | 2θ(°) | 5.445 | 5.328 |
|  | Height (%)* | 100 | 100 |
|  | Full width at half-maximum (°) | 0.397 | 0.347 |
| Second peak | 2θ(°) | 5.959 | 5.86 |
|  | Height (%)* | 97.8 | 91.6 |
|  | Full width at half-maximum (°) | 0.445 | 0.347 |
| Third peak | 2θ(°) | 6.352 | 6.353 |
|  | Height (%)* | 71 | 63.4 |
|  | Full width at half-maximum (°) | 0.383 | 0.329 |

*Height where the highest peak is set as 100%

TABLE 2

|  |  | Crystal 3 | Crystal 4 | Crystal 5 |
|---|---|---|---|---|
| First peak | 2θ (°) | 5.034 | 5.054 | 5.071 |
|  | Height (%)* | 100 | 39.5 | 100 |
|  | Full width at half-maximum (°) | 0.133 | 0.163 | 0.156 |
| Second peak | 2θ (°) | 5.819 | 5.327 | 5.862 |
|  | Height (%)* | 77.5 | 92 | 78.9 |
|  | Full width at half-maximum (°) | 0.145 | 0.293 | 0.164 |
| Third peak | 2θ (°) | 6.373 | 5.877 | 6.416 |
|  | Height (%)* | 35.7 | 100 | 40.2 |
|  | Full width at half-maximum (°) | 0.149 | 0.18 | 0.186 |
| Fourth peak | 2θ (°) | 6.592 | 6.371 | 6.649 |
|  | Height (%)* | 33.8 | 66 | 40.8 |
|  | Full width at half-maximum (°) | 0.115 | 0.274 | 0.163 |
| Fifth peak | 2θ (°) | 7.41 | 9.628 | 7.471 |
|  | Height (%)* | 7.3 | 4.9 | 9.4 |
|  | Full width at half-maximum (°) | 0.343 | 0.097 | 0.241 |
| Sixth peak | 2θ (°) | 9.173 | 10.727 | 9.216 |
|  | Height (%)* | 5.3 | 5.2 | 7.6 |
|  | Full width at half-maximum (°) | 0.251 | 0.373 | 0.135 |
| Seventh peak | 2θ (°) | 19.127 | 29.391 | 19.167 |
|  | Height (%)* | 6.2 | 4.2 | 8.9 |
|  | Full width at half-maximum (°) | 0.129 | 0.187 | 0.348 |

*Height where the highest peak is set as 100%

As arundic acid calcium salt, a compound represented by the following formula:

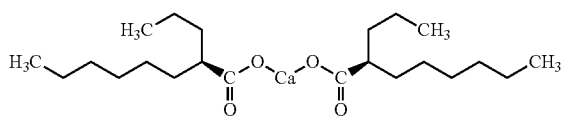

is preferable.

The pharmaceutically acceptable salts of arundic acid can be produced according to the method described in Patent Literature 2, or the synthesis method for arundic acid salts described later.

Examples of solvents for forming the pharmaceutically acceptable salts and solvates of arundic acid include, but are not limited to, water, ethanol, acetone, acetic acid, 1-propanol, 2-propanol, ethyl acetate, diethyl ether, and the like. The solvent is preferably water, ethanol, or a mixture thereof; and more preferably water.

The phrase "comprising, in combination," as used herein is used with meanings including the following cases for the composition of the present invention:

(i) component (A) and component (B) are contained in the form of a mixture in the same preparation (combination preparation);

(ii) component (A) alone or a preparation containing component (A), and component (B) alone or a preparation containing component (B), are individually packaged as separate preparations, sold as a combination (a kit), and used in combination at the time of use;

(iii) component (A) alone or a preparation containing component (A), and component (B) alone or a preparation containing component (B), are separate preparations, sold in combination as a package, and used in combination at the time of use; or (iv) component (A) alone or a preparation containing component (A), and component (B) alone or a preparation containing component (B), are individually packaged as separate preparations, marketed through separate distribution channels, and used in combination at the time of use.

More specifically, the "composition comprising a combination" of the present invention may be used in such a manner that component (A) alone or a preparation containing component (A), and component (B) alone or a preparation containing component (B) are administered to a subject for administration at different times, at the same time, or in parallel, regardless of what forms component (A) alone and component (B) take during the distribution stage, including sale. The above usage includes a usage in which component (A) alone or a preparation containing component (A) is administered to a subject for administration before administration of component (B) alone or a preparation containing component (B); and a usage in which component (A) alone or a preparation containing component (A) is administered to a subject for administration after administration of component (B) alone or a preparation containing component (B).

The phrase "preparation containing component (A)" as used herein refers to a preparation containing component (A) in combination with one or more other components, and the phrase "preparation containing component (B)" as used herein refers to a preparation containing component (B) in combination with one or more other components. The preparation containing component (A) and the preparation containing component (B) are respectively distinguished from a preparation consisting of component (A) alone and a preparation consisting of component (B) alone. Examples of the other components include the carriers and additives for preparations described later.

In the case of animals other than humans, the maximum daily dose of component (A) is 30 mg/kg, preferably 10 mg/kg, and more preferably 3 mg/kg in the amount of component (A). The minimum daily dose of component (A) is 0.1 mg/kg, preferably 0.5 mg/kg, and more preferably 1 mg/kg. The range of the daily dose of component (A) may be suitably set based on the values of the maximum dose and the minimum dose.

In the case of humans, the maximum daily dose of component (A) is 135 mg/person, preferably 100 mg/person, more preferably 50 mg/person, even more preferably 40 mg/person, and still even more preferably 10 mg/person in the amount of component (A). The minimum daily dose of component (A) is 0.5 mg/person, preferably 1 mg/person, more preferably 2.5 mg/person, and even more preferably 5 mg/person. The range of the daily dose of component (A) may be suitably set based on the values of the maximum dose and the minimum dose.

Component (A) may be administered once a day at the dose described above. If necessary, the dose may be administered in two, three, four, or five portions a day; and preferably two or three portions a day.

Component (A) can be administered for a length of time necessary for the prevention or treatment of a disease. The administration period is, for example, 1, 4, 10, 20, 30, or 50 weeks or more, from which a more preferable administration period can be suitably selected. Component (A) can be administered daily, every other day, or every three days; and preferably daily. A roughly one-day cessation may be taken every 5 to 7 days.

In the case of animals other than humans, the maximum daily dose of component (B) is 500 mg/kg, preferably 300 mg/kg, and more preferably 100 mg/kg, in the amount of component (B). The minimum daily dose of component (B) is 3 mg/kg, preferably 10 mg/kg, and more preferably 30 mg/kg. The range of the daily dose of component (B) may be suitably set based on the values of the maximum dose and the minimum dose.

In the case of humans, the maximum daily dose of component (B) is 2500 mg/person, preferably 1000 mg/person, more preferably 500 mg/person, and even more preferably 100 mg/person in the amount of component (B). The minimum daily dose of component (B) is 3 mg/person, preferably 10 mg/person, and more preferably 30 mg/person. The range of the daily dose of component (B) may be suitably set based on the values of the maximum dose and the minimum dose.

The dose of component (B) is 0.1 to 500 parts by weight, preferably 1 to 100 parts by weight, more preferably 3 to 50 parts by weight, and even more preferably 10 to 30 parts by weight, per 1 part by weight of the dose of component (A).

Component (B) may be administered once a day at the dose described above. If necessary, the dose may be administered in two, three, four, or five portions a day; and preferably two or three potions a day.

The administration period for component (B) is, for example, 1, 4, 10, 20, 30, or 50 weeks or more, from which a more preferable administration period can be suitably selected. Component (B) can be administered daily, every other day, or every three days; and preferably daily. A roughly one-day cessation may be taken every 5 to 7 days. Component (B) may be administered in the same manner as the administration of component (A).

Component (A) and component (B) may be individually administered alone, or may be administered as a combination preparation containing components (A) and (B); or as preparations containing one or more other components in combination with them (a preparation containing component (A) and a preparation containing component (B)) by, for example, oral administration, intramuscular injection, subcutaneous injection, and/or intravascular administration.

A combination preparation of component (A) and component (B), and a preparation containing component (A) and/or component (B) may be prepared by using component (A) and/or component (B) in combination with one or more suitable carriers or additives for preparations, if necessary. Carriers and additives that can be used when the preparations are prepared are selected according to the dosage form of the preparations. Examples include those that are widely used in typical drugs, such as excipients, binders, disintegrators, lubricants, coloring agents, taste enhancers, flavor enhancers, surfactants, and the like.

When the combination preparation or the preparation is orally administered (including the case in which the combination preparation or the preparation is sublingually administered), the dosage form is not particularly limited. Examples include tablets, powders, granules, capsules (including hard capsules and soft capsules), fluids, pills, suspensions, jelly preparations, emulsions, and the like. When the combination preparation or the preparation is parenterally administered, the dosage form includes injections, drops, suppositories, nasal drops, preparations for transpulmonary administration, and the like.

When the combination preparation or the preparation is prepared in the form of solid oral preparations, such as tablets, powders, granules, pills, and capsules, examples of usable carriers include the following: excipients such as lactose, sucrose, sodium chloride, glucose, urea, starch, calcium carbonate, kaolin, crystalline cellulose, silicic acid, methylcellulose, glycerol, sodium alginate, and gum arabic; binders such as simple syrups, liquid glucose, liquid starch, gelatin solutions, polyvinyl alcohol, polyvinyl ether, polyvinylpyrrolidone, carboxymethylcellulose, shellac, methylcellulose, ethylcellulose, water, ethanol, and potassium phosphate; disintegrators such as dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, and lactose; disintegration inhibitors such as sucrose, stearic acid, cocoa butter, and hydrogenated oils; absorption enhancers such as sodium lauryl sulfate; humectants such as glycerol and starch;

adsorbents such as starch, lactose, kaolin, bentonite, and colloidal silicic acid; lubricants such as purified talc, stearic acid salts, powdered boric acid, and polyethylene glycol; and the like.

The tablets include oral tablets (uncoated tablets, sugar-coated tablets, gelatin-coated tablets, enteric-coated tablets, film-coated tablets, double-layer tablets, and multilayer tablets), chewable tablets (including those that are ingested while being chewed in the mouth), lozenges (including those that are ingested while being dissolved in the mouth, such as troches), sublingual tablets, and buccal tablets.

When the combination preparation or the preparation is prepared in the form of a pill, which is a solid oral preparation, examples of usable carriers include excipients such as glucose, lactose, starch, cacao butter, hydrogenated vegetable oils, kaolin, and talc; binders such as powdered gum arabic, powdered tragacanth, and gelatin; disintegrators such as laminaran and agar; and the like.

When the combination preparation or the preparation is prepared in the form of a capsule, which is a solid oral preparation, it is prepared by mixing the active ingredient(s) with one or more carriers mentioned above; and filling a hard capsule, a soft capsule, or the like with the mixture.

When the combination preparation or the preparation is a liquid preparation, it may take any form, such as a water-based or oil-based suspension, solution, syrup, elixir, or drink, as long as it is in a liquid state; and can be prepared according to a common method, using one or more generally used additives. The container into which the liquid preparation is poured is not limited, as long as it can be hermetically sealed; and may be a glass container, an aluminum container, or a plastic container.

When the combination preparation or the preparation is prepared in the form of an injection, examples of usable carriers include diluents such as water, ethyl alcohol, macrogol, propylene glycol, ethoxylated isostearyl alcohol, polyoxylated isostearyl alcohol, and polyoxyethylene sorbitan fatty acid esters; pH-adjusters such as sodium citrate, sodium acetate, and sodium phosphate; buffers such as dipotassium phosphate, trisodium phosphate, sodium hydrogen phosphate, and sodium citrate; stabilizers such as sodium pyrosulfite, EDTA, thioglycolic acid, and thiolactic acid; saccharides such as mannitol, inositol, maltose, sucrose, and lactose for use as binders in freeze-drying; and the like. In this case, glucose or glycerol may be incorporated in the pharmaceutical preparation in an amount sufficient to prepare an isotonic solution. General solubilizing agents, soothing agents, topical anesthetics, etc., may also be added to the solution. Subcutaneous, intramuscular, and intravenous injections can be prepared according to common methods by adding these carriers.

When the combination preparation or the preparation is prepared in the form of a drop, it can be prepared by dissolving the compound(s) to be administered in an isotonic electrolyte infusion preparation, such as physiological saline or Ringer's solution.

When component (A) alone or the preparation containing component (A), and component (B) alone or the preparation containing component (B), are individually packaged as separate preparations and used in combination at the time of use ((ii) and (iv) in the description of the phrase "comprising a combination" described above), component (A) alone or the preparation containing component (A) can be administered before, or in parallel with, administration of component (B) alone or the preparation containing component (B). In another embodiment, component (B) alone or the preparation containing component (B) can be administered before, or in parallel with, administration of component (A) alone or the preparation containing component (A). Of course, component (A) alone or the preparation containing component (A), and component (B) alone or the preparation containing component (B), can also be administered at the same time.

When component (A) alone or the preparation containing component (A) is administered before the start of administration of component (B) alone or the preparation containing component (B), administration of component (A) alone or the preparation containing component (A) can be initiated within the 3-day period immediately before the start of administration of component (B) alone or the preparation containing component (B). Administration of component (A) alone or the preparation containing component (A) can be preferably initiated within the 2-day period immediately before, more preferably within the 24-hour period immediately before, even more preferably within the 12-hour period immediately before, and most preferably within the 3-hour period immediately before, the start of administration of component (B) alone or the preparation containing component (B).

When component (B) alone or the preparation containing component (B) is administered before the start of administration of component (A) alone or the preparation containing component (A), administration of component (B) alone or the preparation containing component (B) can be initiated within the 3-day period immediately before, preferably within the 2-day period immediately before, more preferably within the 24-hour period immediately before, even more preferably within the 12-hour period immediately before, and most preferably within the 3-hour period immediately before, the start of administration of component (A) alone or the preparation containing component (A).

The administration period for component (A) alone or the preparation containing component (A), and the administration period for component (B) alone or the preparation containing component (B) are as described above.

When component (A) alone or the preparation containing component (A) is administered in parallel with administration of component (B) alone or the preparation containing component (B), the administration includes the following embodiments, as described above: (a) administration of component (A) alone or the preparation containing component (A), and administration of component (B) alone or the preparation containing component (B), are initiated at the same time; (b) administration of component (A) alone or the preparation containing component (A) is initiated before the start of administration of component (B) alone or the preparation containing component (B); and (c) administration of component (B) alone or the preparation containing component (B) is initiated before the start of administration of component (A) alone or the preparation containing component (A). It is preferable that (a) administration of component (A) alone or the preparation containing component (A), and administration of component (B) alone or the preparation containing component (B), are initiated at the same time. The phrase "administered in parallel" as used herein means that a state in which component (A) and component (B) derived from different preparations are present together in the body is formed, regardless of whether the preparations are administered at the same time. For example, if component (B) alone or the preparation containing component (B) is administered after the start of administration of component (A) alone or the preparation containing component (A), when administration of component (B) alone or the preparation containing component (B) forms a state in which component (B) is present together with component (A) present in the body from an earlier point, component (A) alone or the preparation containing component (A), and component (B) alone or the preparation containing component (B) can be described as being administered in parallel.

The combination preparation in which component (A) and component (B) are contained in the same preparation is a preparation comprising both component (A) and component (B). Further, the combination preparation may be prepared by using these components in combination with one or more carriers or additives for preparations described above.

The ratio of component (A) and component (B) is not particularly limited. For example, the dose of component (B) is 1 to 1000 parts by weight, per 1 part by weight of the dose of component (A). The lower limit is preferably 3, 10, or 30 parts by weight. The upper limit is preferably 100, 300, or 1000 parts by weight.

Depending on the dosage form, the prepared combination preparation may be administered once a day such that the daily doses of component (A) and component (B) fall within the above ranges. If necessary, the prepared combination preparation may be administered in two, three, four, or five portions a day; and preferably two or three portions a day, such that the daily doses fall within the above ranges.

I-2. Pharmaceutical Composition

The combination composition described in Section I-1 above can be used as a pharmaceutical composition. The pharmaceutical composition of this embodiment can be used for the prevention and/or treatment of a neurodegenerative disease such as dementia, Parkinson's disease, amyotrophic lateral sclerosis, Steele-Richardson-Olszewski syndrome, multiple system atrophy, or triplet repeat disease; or cerebral infarction.

In this embodiment, the term "prevention" includes suppressing and/or delaying the onset of symptoms. The term "treatment" includes reducing and/or eliminating existing symptoms.

In this embodiment, the term "dementia" includes Alzheimer's disease; cerebrovascular dementia; frontotemporal dementia such as Pick's disease; dementia with Lewy bodies; and dementia resulting from infections (e.g., spirochete, HIV virus, and prion). The term "dementia" also includes mild cognitive disorders such as MCI. The dementia is preferably a mild cognitive disorder, Alzheimer's disease, or cerebrovascular dementia.

In this embodiment, the term "multiple system atrophy" includes striatonigral degeneration, olivopontocerebellar atrophy, Shy-Drager syndrome, and the like. The multiple system atrophy is preferably olivopontocerebellar atrophy.

In this embodiment, the "triplet repeat disease" includes Huntington's disease, Friedreich's ataxia, spinocerebellar ataxia type 1, and the like.

In this embodiment, the term "cerebral infarction" refers to a state in which neurons and/or glial cells are dead, or can die, as a result of ischemia of brain tissue. In this embodiment, the term "cerebral infarction" includes cerebral infarction from the subacute phase to the chronic phase, and persistent cerebral infarction. Preferable examples of the "cerebral infarction" in this embodiment are cerebral infarction from the subacute phase to the chronic phase, and persistent cerebral infarction.

Furthermore, the pharmaceutical composition of this embodiment can be used for ameliorating a learning disorder. The term "learning disorder" means that inputting a new memory and/or retrieving (recalling) an input memory is not performed in a normal manner. In this embodiment, the "learning disorder" is preferably a spatial cognitive impairment, a memory disorder, or a nonverbal learning disorder; and more preferably a spatial cognitive impairment.

The dose, administration method, and pharmaceutical form of the pharmaceutical composition of this embodiment are as described in Section I-1 above.

I-3. Food composition

The combination composition described in Section I-1 above can be used as a food composition. The dose and administration method of the food composition of this embodiment are as described in Section I-1 above. The dosage form of the food composition of this embodiment is as described in Section I-1 above regarding the combination preparation or preparation for oral administration. Further, the terms "dose" and "administration method" can be read as "intake" and "ingestion method," respectively.

The food composition of this embodiment includes general food and food with health claims (food with function claims, food with nutrient function claims, food for specified health uses). The definition and classification of food with health claims are in accordance with those prescribed by the Health Promotion Act and the Food Sanitation Act in Japan.

The food composition of this embodiment can be used in applications similar to those in which the pharmaceutical composition described in Section I-3 above can be used. If the domestic laws of a country prohibit the use, for the food or drink composition, of a statement concerning the relationship between the composition and a disease, the statement concerning the relationship with the disease can be changed so as not to violate the domestic laws. For example, an expression, such as "for keeping the brain young," "for keeping the brain healthy," "for preventing memory loss," "for restoring memory," "for preventing memory decline," or "for preventing adults (in particular, elderly persons) from getting lost," may be indicated as a use of the food composition.

1-4. Arundic Acid, Pharmaceutically Acceptable Salt Thereof, and Pharmaceutically Acceptable Solvate Thereof The present invention further includes a composition comprising at least one member selected from the group consisting of arundic acid, pharmaceutically acceptable salts thereof, and pharmaceutically acceptable solvates thereof, the composition being used in combination with at least one member selected from the group consisting of TRH analogs, pharmaceutically acceptable salts thereof, and hydrates thereof. The entire description regarding the combination composition and use of the combination composition in Sections 1-1 to I-3 above are incorporated by reference for the composition in this section.

II. Arundic Acid Salt, Production Method Therefor, and Use of Arundic Acid Salt

II-1. Arundic Acid Salt

The arundic acid salt according to this embodiment is, for example, a salt represented by Formula (II) below:

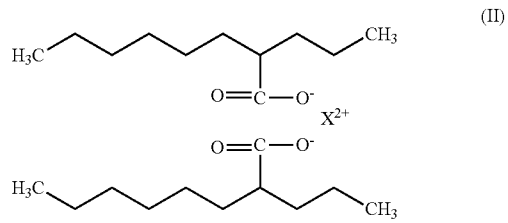

wherein $X^{2+}$ is a divalent cation.

The pharmaceutically acceptable salt of arundic acid is preferably a compound of Formula (II) above. Among the compounds of Formula (II), a compound in which $X^{2+}$ is $Ca^{2+}$, $Mg^{2+}$, $Fe^{2+}$, $Ba^{2+}$, $^+H_3N-NH_3^+$, $^+H_2N=NH_2^+$, or $^+HN\equiv NH^+$ is preferable; and a compound in which $X^{2+}$ is $Ca^{2+}$ is particularly preferable.

The pharmaceutically acceptable salt of arundic acid include enantiomers, those in an amorphous form, and those in a crystalline form. In particular, when $X^{2+}$ is $Ca^{2+}$, the salt is preferably crystalline. Further, the crystals are preferably those stated in Section I-1 above.

Examples of solvents for forming pharmaceutically acceptable salts and solvates of arundic acid include, but are not limited to, water, ethanol, acetone, acetic acid, 1-propanol, 2-propanol, ethyl acetate, diethyl ether, and the like. The solvent is preferably water, ethanol, or a mixture thereof; and more preferably water.

II-2. Method for Synthesizing Salt Represented by Formula (II)

The method for synthesizing the salt represented by Formula (II) is not limited, as long as the salt can be synthesized.

For example, the salt can be synthesized by allowing a divalent cation to act on the arundic acid described in Section I-1 above.

Specifically, the arundic acid described in Section I-1 above is dissolved in about 0.1 to 1.5 N aqueous sodium hydroxide solution, and the resulting solution is then mixed with about 0.5 to 2 M calcium chloride to form a solid. From the solid, the solvent component is removed, optionally followed by washing and drying, thereby obtaining an arundic acid salt.

In another embodiment, the arundic acid is dissolved in a lower alcohol (such as methanol or ethanol), and calcium carbonate is added in an equivalent amount to the solution. The precipitated calcium salt is separated by filtration, and washed with alcohol. The precipitated calcium salt is dissolved again in purified water. After the purified water is evaporated, the calcium salt is washed with alcohol to obtain a recrystallized product. In the present specification, an equivalent (e.g.) refers to the amount of a base (mol) with which 1 mol of the carboxyl group of arundic acid can be just neutralized.

Further, in another embodiment, the arundic acid described in Section I-1 above is dissolved in about 0.1 to 1.5 N aqueous sodium hydroxide solution, and the resulting solution is then mixed with aqueous ammonia. The solvent component is removed to obtain a solid component, optionally followed by washing and drying the solid component, thereby obtaining an arundic acid salt.

In another embodiment, for example, the arundic acid described in Section I-1 above is mixed with about 0.4 to 0.6 equivalents of calcium hydroxide in a solvent, such as methyl tert-butyl ether, acetonitrile, or dichloromethane; preferably methyl tert-butyl ether. The mixture is heated to, for example, about 40 to 60° C., and maintained at this elevated temperature for about 12 to 24 hours. The temperature is then lowered to room temperature (about 18 to 32° C.), and the mixture is maintained at this lowered temperature for about 0.5 to 2 hours. After the mixture is maintained in such a manner, the mixture becomes a suspension; and calcium salt, which is a solid component, can be obtained by centrifugation. Moreover, the supernatant after centrifugation may be dried to obtain calcium salt as a solid component. Calcium salt synthesized by this method is equal to crystal 1 described in Section I-1 above.

Arundic acid salt synthesized by a method described above may be further recrystallized. The recrystallization may be performed by the evaporation method or the slurry method, preferably the slurry method. Arundic acid salt is suspended in, for example, acetonitrile or water at room temperature (about 18 to 32° C.) and stirred for about 0.5 to 1 hour. Thereafter, the solvent, if the solvent is acetonitrile, is evaporated at room temperature (about 18 to 32° C.), preferably about 23 to 28° C., for about 16 to 24 hours. If the solvent is water, the water is evaporated at about 20 to 55° C. for about 16 to 72 hours. When acetonitrile is used as a solvent, crystal 2 described in Section I-1 above is obtained. When water is used as a solvent, and evaporation is performed at 20 to 40° C., crystal 4 or 5 described in Section I-1 above is obtained. When water is used as a solvent, and evaporation is performed at 45 to 55° C., crystal 3 described in Section I-1 above is obtained.

II-3. Composition Comprising Salt Represented by Formula (II) or Pharmaceutically Acceptable Solvate Thereof This embodiment relates to a composition comprising a salt represented by Formula (II) described in Section II-1 above, or a pharmaceutically acceptable solvate thereof. This embodiment includes a composition comprising a salt represented by Formula (II) described in Section II-1 above, or a pharmaceutically acceptable solvate thereof, the composition being used in combination with at least one member selected from the group consisting of TRH analogs, pharmaceutically acceptable salts thereof, and hydrates thereof.

The dose, administration method, pharmaceutical form, etc., of the composition of this embodiment are as described in Section I-1 above regarding component (B). For the combination of the composition comprising a salt represented by Formula (II) described in Section II-1 above or a pharmaceutically acceptable solvate thereof, and at least one member selected from the group consisting of TRH analogs, pharmaceutically acceptable salts thereof, and hydrates thereof, the description relating to the combination composition in Section I-1 above is incorporated by reference in this section.

II-4. Pharmaceutical Composition

The composition described in Section II-3 above can be used as a pharmaceutical composition. The pharmaceutical composition can be used in, for example, the applications described in Patent Literature 2; and the treatment and/or prevention of other cranial nerve system diseases.

Specifically, the pharmaceutical composition of this embodiment can be used for improving the function of astrocytes, or changing reactive astrocytes to astrocytes.

The pharmaceutical composition of this embodiment can be used for the treatment and/or prevention of a neurodegenerative disease, neurological dysfunction after brain and spinal cord traumatic injury, brain tumor, cerebrospinal disease associated with infection, or multiple sclerosis. The "neurodegenerative disease" in this embodiment is as described in Section I-2 above. The neurodegenerative disease is preferably dementia, Parkinson's disease, amyotrophic lateral sclerosis, Steele-Richardson-Olszewski syndrome, or multiple system atrophy. The "brain tumor" in this embodiment is a glioma derived from glial cells, and preferably an astrocytoma. The "cerebrospinal disease associated with infection" in this embodiment is not limited, as long as it is a disease that develops in association with microbial infection. The cerebrospinal disease associated with infection is preferably meningitis, brain abscess, Creutzfeldt-Jakob disease, or cerebrospinal disease associated with AIDS.

The "prevention" and "treatment" in this embodiment are as described in Section I-2 above.

The dose, administration method, pharmaceutical form, etc., of the pharmaceutical composition of this embodiment are as described in Section I-1 above regarding component (B).

II-5. Food Composition

The composition described in Section II-2 above can be used as a food composition. The dose and administration method of the food composition of this embodiment are as described in Section I-1 above regarding component (B). The dosage form of the food composition of this embodiment is as described in Section I-1 above regarding the preparation of component (B) orally administered. Further, the terms "dose" and "administration method" can be read as "intake" and "ingestion method," respectively.

The food composition of this embodiment includes general food, and food with health claims (food with function claims, food with nutrient function claims, food for specified health uses). The definition and classification of food with health claims are in accordance with those prescribed by the Health Promotion Act and the Food Sanitation Act in Japan.

The food composition of this embodiment can be used in applications similar to those in which the pharmaceutical composition described in Section II-4 above can be used. If the domestic laws of a country prohibit the use, for the food or drink composition, of a statement concerning the relationship between the composition and a disease, the statement concerning the relationship with the disease can be changed so as not to violate the domestic laws. For example, an expression, such as "for performing activities of daily living smoothly," "for decreasing memory loss," "for making it easy for words to be vocalized," or "for reducing the number of times adults (in particular, elderly persons) get lost," may be indicated as a use of the food composition.

EXAMPLES

The present invention is described more specifically below with reference to Examples. However, the present invention is not limited thereto or thereby.

I. Example 1

2. Experimental Method
1) Animals Used 7-week-old (body weight: 200 to 240 g) male Crl: Wistar rats were used for an experiment after acclimation for 1 week or more. During the experimental period, the rats were raised in an animal room maintained at a room temperature of 23±1° C. and a humidity of 55±5%, and illuminated for 12 hours (6:30-18:30); with ad libitum access to food (Oriental Yeast, CRF-1) and water.

2) Drugs Used

Arundic acid ((R)-(−)-2-propyloctanoic acid: Lot No. CS04818-503, M.W.186.29, specific gravity: 0.908), which is an astrocyte function-improving agent, used in this test is a product synthesized by Chemical Soft Co., Ltd. Taltirelin hydrate (hereinafter referred to as taltirelin, M.W.463.47: N-[(4S)-1-methyl-2,6-dioxohexahydropyrimidine-4-carbonyl]-L-histidyl-L-prolinamide (Lot No. N16P)), which is a ataxia-improving agent, used in this test is a product purchased from Matrix Scientific. When arundic acid was to be administered at a dose of 30 mg/kg/5 mL, 1.61 mL of 1N NaOH was added to 300 mg (306 μL) of arundic acid to dissolve the arundic acid, and 48.084 mL of water or 0.5% CMC (carboxymethyl cellulose) was added to the resulting solution to make a total volume of 50 mL. In the experiment, a 10-fold concentrated arundic acid solution was prepared and adjusted for the concentration before use. When taltirelin was to be administered at a dose of 3 mg/kg or 10 mg/kg, taltirelin was dissolved in distilled water in a volume of 5 ml/kg. The test drug(s) were orally administered for 28 days (including Saturdays, Sundays, and public holidays), starting from 1 week after preparation of four-vessel occlusion models.

3) Experimental Groups

Five groups of rats (4 to 6 rats per group) were used. The details are as follows. Group 1 is a group that was not subjected to four-vessel occlusion. Groups 2 to 5 are groups that were subjected to four-vessel occlusion.
Group 1: Sham control (distilled water 2 ml/kg/day) group
Group 2: Control (distilled water 5 ml/kg/day) group
Group 3: Arundic acid (30 mg/kg/day) administration group
Group 4: Taltirelin (10 mg/kg/day) administration group
Group 5: Arundic acid (10 mg/kg/day)/taltirelin (3 mg/kg/day) combination group 2. Method of Producing Four-Vessel Occlusion Model
1) Vertebral Artery Cauterization Surgery A vertebral artery cauterization surgery was performed in accordance with the method of Pulsinelli & Brierley (Pulsinelli, W. A. and Brierley, J. B.: Stroke 10, 267, 1979). More specifically, the rats anesthetized with Nem-ravona (registered trademark) and Butal (registered trademark) were fixed in the prone position to a brain stereotaxic apparatus, and the dorsal cervical skin and muscle layer were incised to expose the first cervical vertebra. The tips of the tweezers of a bipolar coagulator (Mizuho Ikakogyo Co., Ltd.; MICROID) were inserted into the alar foramina on both sides of the first cervical vertebra, and the vertebral artery running upward toward the cerebral base was bilaterally cut off by electrocauterization. The skin was then sutured. Subsequently, the rats were fixed again in the supine position to an experimental surgical table, and the ventral cervical skin was incised. After the bilateral common carotid arteries were separated from surrounding tissues and silk thread was looped around the arteries, the skin was sutured. After completion of the surgery, the rats were returned to a cage and observed. No behavioral abnormality was confirmed.

2) General Condition Observation After Common Carotid Artery Occlusion and Restoration of Blood Flow Twenty-four hours after vertebral artery cauterization by the above method, the rats under isoflurane inhalation anesthesia were fixed in the supine position for immobilization before common carotid artery ligation on the following day. The ventral cervical skin was incised again to expose bilateral common carotid arteries. First, the right-side common carotid artery was occluded with an artery clamp or Mosquito hemostat forceps (both forceps were covered with a silicone tube to reduce stimulus to the blood vessel wall). After about 60 seconds, the left-side common carotid artery was occluded in the same manner. Since righting reflex (RR) of rats during bilateral common carotid artery occlusion, i.e., rats with brain ischemia, was lost, immobilization in the supine-position seemed unnecessary. However, sudden movements, such as walking-like motions of four limbs or lateral turning, were observed. Since such movements may cause forceps to excessively pull the blood vessel, the rats with brain ischemia remained fixed in the supine position. After 10 minutes of brain ischemia, the forceps were removed. After restoration of blood flow was confirmed by direct observation, the rats were promptly released from immobilization in the supine position, and placed gently into an observation box. For this experiment, animals after ischemia with a loss of righting reflex, and then with normal behaviors, were used (n=4 to 6 rats per group).

3. Experimental Device and Experimental Settings in Morris Water Maze Test

A Morris water maze test was performed by using a circular pool (168 cm in diameter and 40 cm in depth) filled with water, and a platform (10 cm in diameter and 30 cm in height) for escape of rats. In Zone 3, one transparent plastic escape platform (10 cm in diameter and 30 cm in height) was set at a location 40 cm away from the center of the pool, and 23 cm away from the periphery of the pool. The water temperature of the water maze during the experiment was kept at 23° C. (±1.5° C.). A Hidden test was performed at the time of grouping 1 week after four-vessel occlusion, and on the day following the final administration of test drugs. For the Hidden test, the pool was filled with water to a height of 1 cm above the platform (water depth: 31 cm). A Transfer test was performed 3 days after the final administration of test drugs. For the Transfer test, the platform was removed, and the pool was filled with water to a water depth of 31 cm. To enable the rats to memorize surrounding various spatial arrangements, cues, such as posters and photographs, were placed on the wall. The cues always remained at the same locations during the experiment (FIG. 1: a plan view of Morris water maze, and the laboratory layout).

In FIG. 1, Zone 1 to Zone 4 show four quadrants of the circular pool. E, W, S, and N represent the directions of east, west, south, and north. An experimenter observed the rats from the S position.

A CCD camera was set at the center of the water maze, and a personal computer connected to the CCD camera automatically sensed the white color of the rats' fur and analyzed their swimming trajectory.

4. Experimental Schedule

Figure 2:
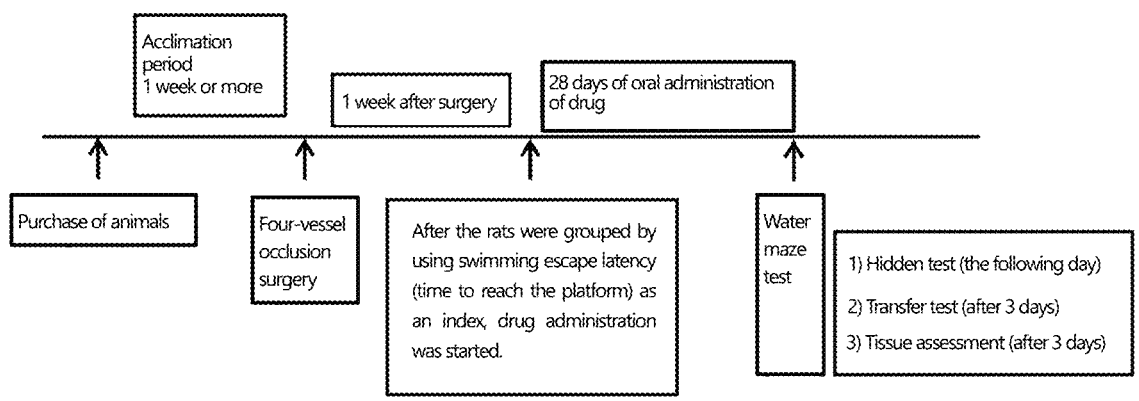
FIG. 2 is a diagram showing an experimental schedule.

FIG. 2 shows an experimental schedule.

More specifically, an experiment was performed according to the following procedures.

1) Forty 8-week-old (body weight: 200 to 240 g) male Crl:Wistar rats were purchased. Their body weight was measured at the time of purchase. The acclimation period was 1 week or more.

2) After a four-vessel occlusion surgery (24 hours after vertebral artery cauterization, 10 minutes of common carotid artery occlusion), blood flow was restored, and general conditions were then observed.

3) One week after restoration of blood flow, 5 trials of the Hidden test according to the Morris water maze test were performed with intervals of 30 minutes, and a cut-off time of 180 seconds. The rats were grouped by using swimming escape latency (time to reach the platform) as an index. After grouping, oral administration of the drug(s) was started.

4) The drug(s) were orally administered for 28 days.

5) On the day following the final administration of the drug, 5 trials of the Hidden Test for assessing spatial memory by using a water maze were performed with intervals of 30 minutes, and a cut-off time of 180 seconds. After 30 minutes, the platform was removed, and a Transfer test was performed with the pool being filled with water to a water depth of 31 cm.

From the starting point in Zone 1, the rats were thrown into a water maze with their heads being directed toward the outside of the water maze. The location of the platform was fixed at a point (corresponding to E in FIG. 1) on the east side in the water maze (corresponding to Zone 3 in FIG. 1). The maximum time of one trial was 180 seconds. When a rat reached the platform within 180 seconds, the rat was allowed to stand on the platform for 15 seconds. When a rat did not reach the platform even after 180 seconds, the experimenter guided the rat to the platform by hand, and allowed the rat to stand there for 15 seconds. This rat was expected to learn the location of the platform by using surrounding various spatial arrangements as cues during the 180 seconds of the Hidden test and 15 seconds of being allowed to stand on the platform (Hidden test). In the Hidden test, swimming trajectory to the goal, swimming distance, swimming escape latency (time to reach the platform), and average swimming speed were measured per trial.

Three days after the final administration of the test drug, the platform was removed and a Transfer test in which the pool was filled with water to a water depth of 31 cm was performed. This is a test in which the rats were allowed to swim freely in a state in which the platform, which was the goal in the Hidden test, had been removed; and the length of time for which each rat swam in the region where the platform previously existed (corresponding to Zone 3 in FIG. 1) was checked. Each rat was given only one trial, and the time was 180 seconds. The starting point was on the side opposite to the platform (see FIG. 1). In the Transfer test, the time spent in each Zone and the number of times the rats crossed over the platform location were determined.

The behaviors of the rats in each trial were automatically analyzed with a CCD camera and the SMART (produced by Kyoto L Giken) behavioral analysis program by binarization of the white color of rats' fur and black ash color of the surrounding area.

Significant differences between the groups in spatial memory according to the Morris water maze method were determined by the nonparametric Dunnett's multiple comparison test. 6) After completion of the Morris water maze test, the brain of each rat was perfusion-fixed with 4% paraformaldehyde. The details are as follows.

(1) Production of 4% Paraformaldehyde Phosphate Buffer 400 mL of distilled water was added to 40 g of paraformaldehyde to dissolve the paraformaldehyde using a heating stirrer. 1N NaOH was then added dropwise to the solution until the resulting mixture became transparent. After dissolution, distilled water was added to the solution in a measuring cylinder to make a total volume of 500 mL. Before use, 100 mL of a commercially available phosphate buffered physiological saline (PBS) (10-fold concentration) was added to make a total volume of 1000 mL.

(2) Brain Perfusion Fixation

After completion of the Transfer test, the rats were anesthetized, and the chest cavity was opened to expose the heart. A ventricle was incised to insert a catheter from the heart to the carotid artery, and 50 mL or more of heparinized physiological saline was perfused. Subsequently, 50 mL or more of 4% paraformaldehyde phosphate buffer was perfused. The perfusion procedures were performed with ligation of the main artery. After perfusion-fixation, the brain was removed and immersion-fixed in 4% paraformaldehyde phosphate buffer.

(3) HE staining

20-μm serial thick frozen sections were prepared from this brain using a cryostat. Alternating serial sections were stained with hematoxylin-eosin. The degree of neuronal death in the stained tissue was semi-quantitatively evaluated under an optical microscope.

7) Using the data obtained in the Morris water maze test, a comparison between two groups was performed by Dunnett's multiple comparison method to calculate p value.

5. Results

Table 3 shows body weight changes in each rat during the test. Day 0 refers to one week after the four-vessel occlusion surgery (restoration of blood flow).

TABLE 3

| | Body weight changes (Mean ± S.E., Unit: g) | | | | |
| --- | --- | --- | --- | --- | --- |
| | Before administration | After administration | | | |
| Group | Day 0 | Day 7 | Day 14 | Day 21 | Day 28 |
| 1 | 241.6 ± 5.2 | 264.6 ± 5.7 | 277.4 ± 6.1 | 292.0 ± 7.8 | 314.3 ± 8.1 |
| 2 | 228.1 ± 3.8 | 234.8 ± 4.1 | 250.1 ± 4.8 | 279.3 ± 5.1 | 303.5 ± 6.4 |
| 3 | 228.7 ± 4.9 | 255.5 ± 5.1 | 272.6 ± 7.4 | 288.0 ± 7.1 | 308.5 ± 5.0 |
| 4 | 228.6 ± 4.5 | 256.6 ± 8.7 | 272.3 ± 10.3 | 291.3 ± 12.0 | 307.2 ± 12.2 |
| 5 | 224.8 ± 3.7 | 257.7 ± 4.9 | 269.0 ± 6.2 | 287.4 ± 7.8 | 318.7 ± 8.6 |

Table 4 shows the Morris water maze test results of the rats at the time of grouping and after administration of test drugs for 28 days.

TABLE 4

| Group | At the time of grouping Latency (sec) | Hidden test Latency (sec) | Hidden test Total distance moved (m) | Transfer test Residence time in Zone 3 (sec) | Transfer test Platform Crossing Times |
|---|---|---|---|---|---|
| 1 | 67.4 | 38.6 | 7.7 | 113.2 | 18 |
|   | 75 | 56.2 | 12.9 | 93.4 | 10 |
|   | 49.2 | 34.2 | 7.0 | 74.6 | 8 |
|   | 57.6 | 43.2 | 7.7 | 109.3 | 9 |
|   | 61.3 | 47.2 | 11.5 | 93.7 | 12 |
|   | 68.1 | 31.4 | 5.3 | 102.1 | 16 |
| Mean ± S.E. | 63 ± 3.7 | 42 ± 3.7* | 8.7 ± 1.2** | 98 ± 5.7** | 12.2 ± 1.6* |
| 2 | 102 | 87 | 18.4 | 57.7 | 5 |
|   | 96.1 | 79.5 | 19.3 | 36.0 | 4 |
|   | 125.4 | 100.1 | 22.3 | 43.8 | 3 |
|   | 81.9 | 97.9 | 19.6 | 44.3 | 3 |
| Mean ± S.E. | 101 ± 9.1 | 91 ± 4.8 | 19.9 ± 0.8 | 46 ± 4.5 | 3.8 ± 0.5 |
| 3 | 112.5 | 73.8 | 13.0 | 82.9 | 6 |
|   | 86.9 | 82.2 | 15.8 | 66.0 | 9 |
|   | 123.2 | 90.3 | 17.9 | 43.6 | 2 |
|   | 87 | 66.5 | 22.8 | 55.2 | 5 |
| Mean ± S.E. | 102 ± 9.2 | 78 ± 5.2 | 17.4 ± 2.1 | 62 ± 8.4 | 5.5 ± 1.4 |
| 4 | 100.1 | 68.9 | 19.8 | 58.5 | 8 |
|   | 97.2 | 88.1 | 15.0 | 66.9 | 7 |
|   | 85.5 | 76.4 | 12.3 | 47.1 | 4 |
|   | 124.8 | 99.1 | 17.1 | 56.0 | 2 |
| Mean ± S.E. | 102 ± 8.3 | 83 ± 6.6 | 16.1 ± 1.6 | 57 ± 4.1 | 5.3 ± 1.4 |
| 5 | 106.4 | 41.8 | 8.5 | 97.4 | 13 |
|   | 88.9 | 32.1 | 7.00 | 101.4 | 11 |
|   | 98.3 | 33.1 | 16.5 | 70.6 | 9 |
|   | 111.6 | 59.5 | 11.2 | 70.9 | 8 |
| Mean ± S.E. | 101 ± 5.0 | 42 ± 6.3* | 10.8 ± 2.1* | 85 ± 8.3* | 10.3 ± 1.1* |

*indicates p < 0.05 relative to Group 2.
**indicates p < 0.01 relative to Group 2.

Next, Table 5 show the Hidden test and Transfer test results of each group after test drug administration.

TABLE 5

| Group | One group (number of rats) | Hidden test Latency (sec) | Hidden test Distance (m) | Transfer test Residence time in Zone 3 (sec) | Transfer test Platform Crossing Times |
|---|---|---|---|---|---|
| 1 | 6 | 42 ± 3.7* | 8.7 ± 1.2** | 98 ± 5.7** | 12.2 ± 1.6* |
| 2 | 4 | 91 ± 4.8 | 19.9 ± 0.8 | 46 ± 4.5 | 3.8 ± 0.5 |
| 3 | 4 | 78 ± 5.2 | 17.4 ± 2.1 | 62 ± 8.4 | 5.5 ± 1.4 |
| 4 | 4 | 83 ± 6.6 | 16.1 ± 1.6 | 57 ± 4.1 | 5.3 ± 1.4 |
| 5 | 4 | 42 ± 6.3* | 10.8 ± 2.1* | 85 ± 8.3* | 10.3 ± 1.1* |

*indicates p < 0.05 relative to Group 2.
**indicates p < 0.01 relative to Group 2.

Further, Table 6 shows the time each group spent in each Zone in the Transfer test after test drug administration. Table 7 shows the average swimming speed.

TABLE 6

| Group | Zone 1 | (%) | Zone 2 | (%) | Zone 3 | (%) | Zone 4 | (%) |
|---|---|---|---|---|---|---|---|---|
| 1 | 21.6 | 11.9 | 24.5 | 13.4 | 113.2 | 62.1 | 22.9 | 12.6 |
|   | 21.6 | 12.6 | 31.7 | 18.5 | 93.4 | 54.4 | 25.1 | 14.6 |
|   | 22.3 | 13.2 | 15.1 | 9.0 | 74.6 | 44.3 | 56.4 | 33.5 |
|   | 33.2 | 15.8 | 46.4 | 22.1 | 109.3 | 52.0 | 21.2 | 10.1 |
|   | 24.3 | 13.7 | 18.9 | 10.7 | 93.7 | 52.9 | 40.1 | 22.7 |
|   | 18.1 | 10.7 | 40.8 | 24.0 | 102.1 | 60.1 | 8.8 | 5.2 |
| Mean ± S.E. | 23.5 ± 2.1 | 13.0 ± 0.7 | 29.6 ± 5.0 | 16.3 ± 2.5 | 97.7 ± 5.7** | 54.3 ± 2.6 | 29.1 ± 6.8 | 16.4 ± 4.1 |
| 2 | 30.7 | 18.2 | 21.5 | 12.8 | 57.7 | 34.2 | 58.6 | 34.8 |
|   | 37.6 | 21.1 | 26.3 | 14.7 | 36.0 | 20.2 | 78.6 | 44.0 |
|   | 35.6 | 19.5 | 63.3 | 34.7 | 43.8 | 24.0 | 39.9 | 21.9 |
|   | 49.4 | 25.7 | 32.8 | 17.1 | 44.3 | 23.0 | 65.8 | 34.2 |

TABLE 6-continued

| Group | Zone 1 | (%) | Zone 2 | (%) | Zone 3 | (%) | Zone 4 | (%) |
|---|---|---|---|---|---|---|---|---|
| Mean ± S.E. 3 | 38.3 ± 4.0 | 21.1 ± 1.6 | 36.0 ± 9.4 | 19.8 ± 5.0 | 45.5 ± 4.5 | 25.4 ± 3.1 | 60.7 ± 8.1 | 33.7 ± 4.6 |
|  | 24.0 | 13.3 | 16.9 | 9.4 | 82.9 | 46.0 | 56.5 | 31.3 |
|  | 32.5 | 19.3 | 34.4 | 20.4 | 66.0 | 39.1 | 35.7 | 21.2 |
|  | 63.9 | 33.3 | 68.2 | 35.5 | 43.6 | 22.7 | 16.4 | 8.5 |
|  | 45.8 | 25.4 | 48.3 | 26.8 | 55.2 | 30.6 | 31.0 | 17.2 |
| Mean ± S.E. 4 | 41.6 ± 8.7 | 22.8 ± 4.3 | 42.0 ± 10.9 | 23.0 ± 5.5 | 61.9 ± 8.4 | 34.6 ± 5.1 | 34.9 ± 83 | 19.6 ± 4.7 |
|  | 24.5 | 13.6 | 63 | 35.1 | 58.5 | 32.6 | 33.6 | 18.7 |
|  | 44.4 | 24.8 | 30.4 | 17.0 | 66.9 | 37.3 | 37.5 | 20.9 |
|  | 38.6 | 21.2 | 29.6 | 16.2 | 47.1 | 25.8 | 67 | 36.8 |
|  | 49.7 | 27.3 | 14.1 | 7.7 | 56 | 30.7 | 62.5 | 34.3 |
| Mean ± S.E. 5 | 39.3 ± 5.4 | 21.7 ± 3.0 | 34.2 ± 10.3 | 19.0 ± 5.8 | 57.1 ± 4.1 | 31.6 ± 2.4 | 50.2 ± 8.5 | 27.6 ± 4.6 |
|  | 16.8 | 9.6 | 33.6 | 19.3 | 97.4 | 55.9 | 26.4 | 15.2 |
|  | 21.9 | 11.3 | 27.2 | 14.0 | 101.4 | 52.2 | 43.8 | 22.5 |
|  | 23.5 | 14.3 | 54 | 32.8 | 70.6 | 42.9 | 16.3 | 9.9 |
|  | 38.8 | 20.8 | 29.6 | 15.9 | 70.9 | 38.0 | 47.3 | 25.3 |
| Mean ± S.E. | 25.3 ± 4.7 | 14.0 ± 2.0 | 36.1 ± 6.1 | 20.5 ± 4.3 | 85.1 ± 7.3* | 47.3 ± 3.0 | 33.5 ± 7.3 | 18.2 ± 3.5 |

*$p < 0.05$ relative to Group 2.
**$p < 0.01$ relative to Group 2.

TABLE 7

| Group | Mean speed (m/s) |
|---|---|
| 1 | 0.19 |
|  | 0.16 |
|  | 0.16 |
|  | 0.13 |
|  | 0.20 |
|  | 0.14 |
| Mean ± S.E. | 0.16 ± 0.01 |
| 2 | 0.21 |
|  | 0.13 |
|  | 0.19 |
|  | 0.14 |
| Mean ± S.E. | 0.17 ± 0.02 |
| 3 | 0.12 |
|  | 0.15 |
|  | 0.20 |
|  | 0.16 |
| Mean ± S.E. | 0.16 ± 0.02 |
| 4 | 0.21 |
|  | 0.13 |
|  | 0.19 |
|  | 0.15 |
| Mean ± S.E. | 0.17 ± 0.02 |
| 5 | 0.19 |
|  | 0.15 |
|  | 0.15 |
|  | 0.22 |
| Mean ± S.E. | 0.18 ± 0.02 |

As shown in Table 3, before administration (on day 0), body weight decrease was observed in Groups 2 to 5; this body weight decrease was presumably due to stress and dysphagia (disorder in the process of recognizing food, carrying the food to the mouth, and chewing and swallowing the food) caused by four-vessel occlusion surgery. As compared with Group 2, Groups 3, 4, and 5 then showed a favorable body weight increase until day 28 after the administration. In particular, the body weight of Group 5 on day 28 was recovered to the same level as that of Group 1. This result suggests that administration of a combination of arundic acid and taltirelin can alleviate stress and dysphagia caused by four-vessel occlusion surgery.

As shown in Table 4, when measured at the time of grouping, the rats in Groups 2 to 5 subjected to four-vessel occlusion surgery took a longer time to reach the platform than the rats in Group 1 not subjected to four-vessel occlusion surgery. The results thus suggest that their location learning capacity decreased. Table 5 shows effects of the test drugs. Group 3 to which only arundic acid was administered, and Group 4 to which only taltirelin was administered showed no improvement in time to reach the platform in the Hidden test; furthermore, these groups were also not considered to be significantly improved in terms of the total distance moved, as compared with Group 2, which is a control group. In contrast, Group 5 to which both arundic acid and taltirelin were administered took a significantly shorter time to reach the platform in the Hidden test, which was as short as the time of Group 1, which is a Sham control group; furthermore, the total distance moved was also significantly short, as compared with that of Groups 2 to 4. This result suggests that administration of a combination of arundic acid and taltirelin can recover the location learning capacity and location memory capacity (spatial learning capacity and spatial memory capacity) lost by four-vessel occlusion.

Further, as shown in Table 5, the combined effect of arundic acid and taltirelin was also observed in the Transfer test. As compared with Group 1, the rats in Groups 2 to 4 spent a shorter time in Zone 3 where the platform was previously located, and crossed over the platform location less frequently. This result suggests that the rats in Groups 2 to 4 failed to recall that the platform was in Zone 3 (i.e., they failed to retrieve the memory). In contrast, the rats in group 5 spent a longer time in Zone 3 than Groups 2 to 4, and crossed over the platform location many times; the number of crossings was close to the value of Group 1. This result suggests that a combination of arundic acid and taltirelin can improve retrieval (recall) of memory. In contrast, the time Groups 2 to 4 spent in Zones 1, 2, and 4 was not significantly reduced (Table 6), and no difference was observed in the average swimming speed among Groups 1 to 5 (Table 7). These suggest that there is no possibility that the four-vessel occlusion surgery reduced motor function. It is thus speculated that the obtained results depend on learning capacity and memory capacity, and that administration of a combination of arundic acid and taltirelin can improve spatial learning capacity and spatial memory capacity assessed in the Morris water maze test.

Figure 3A:
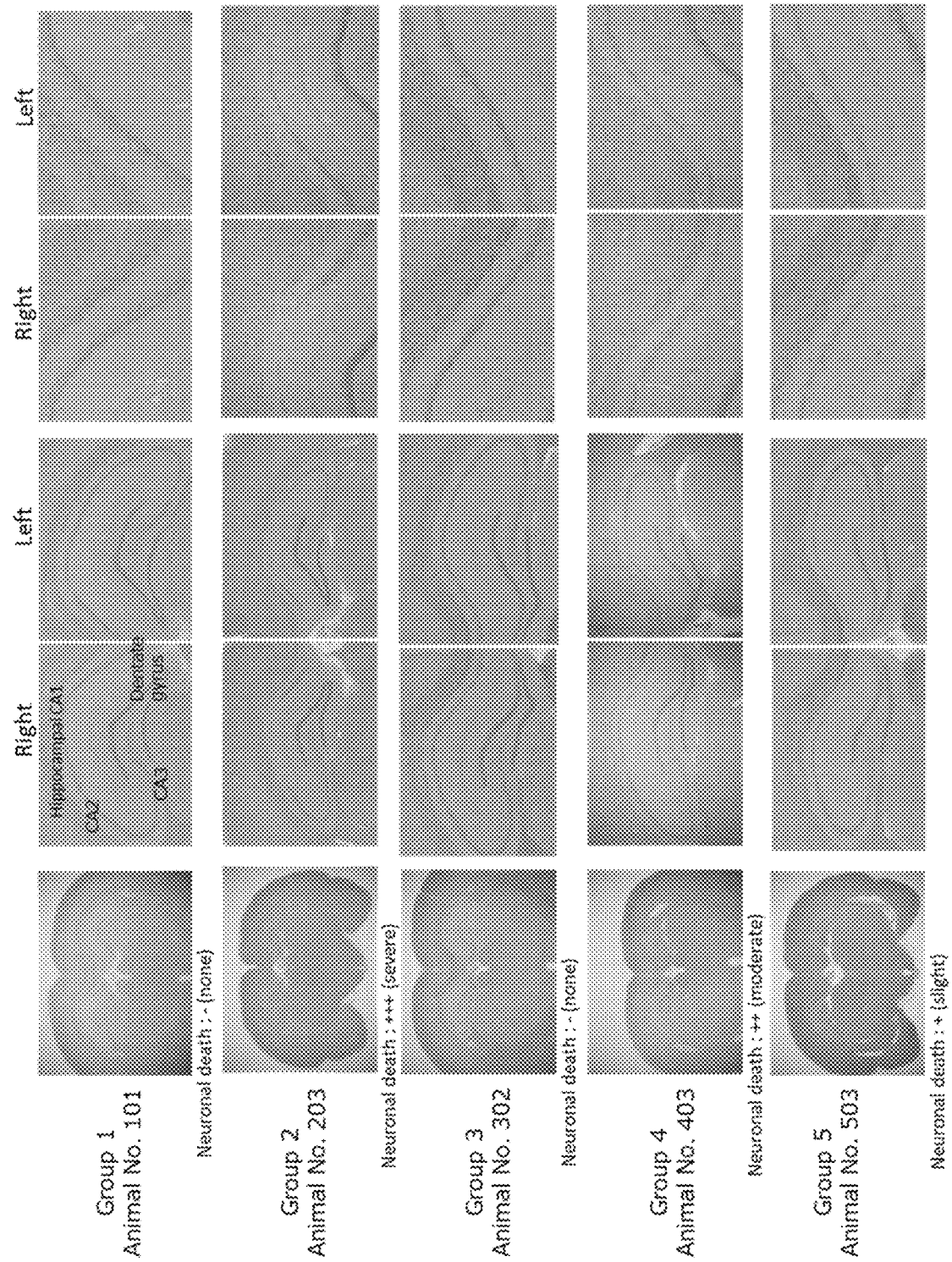
FIG. 3A shows HE staining images of hippocampus CA1 in Groups 1 to 5.
Figure 3B:
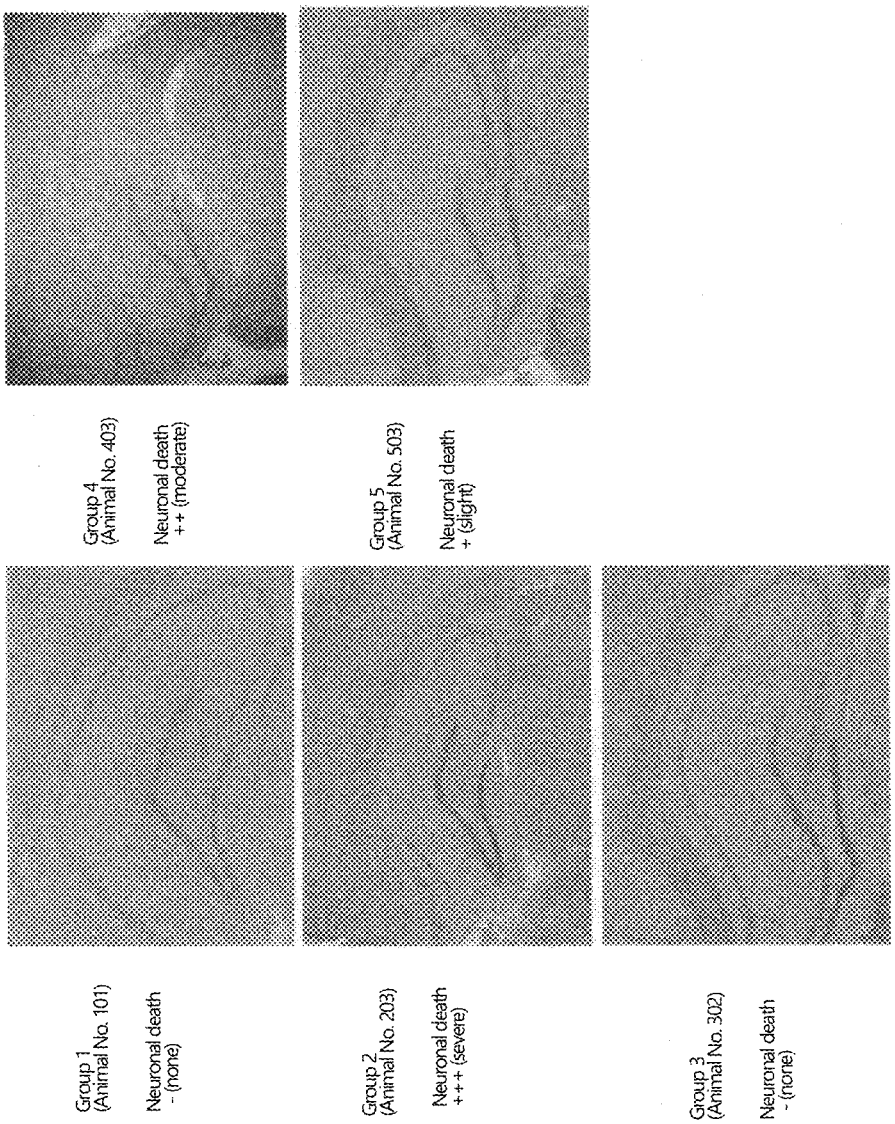
FIG. 3B shows higher magnifications of FIG. 3A.
Figure 3C:
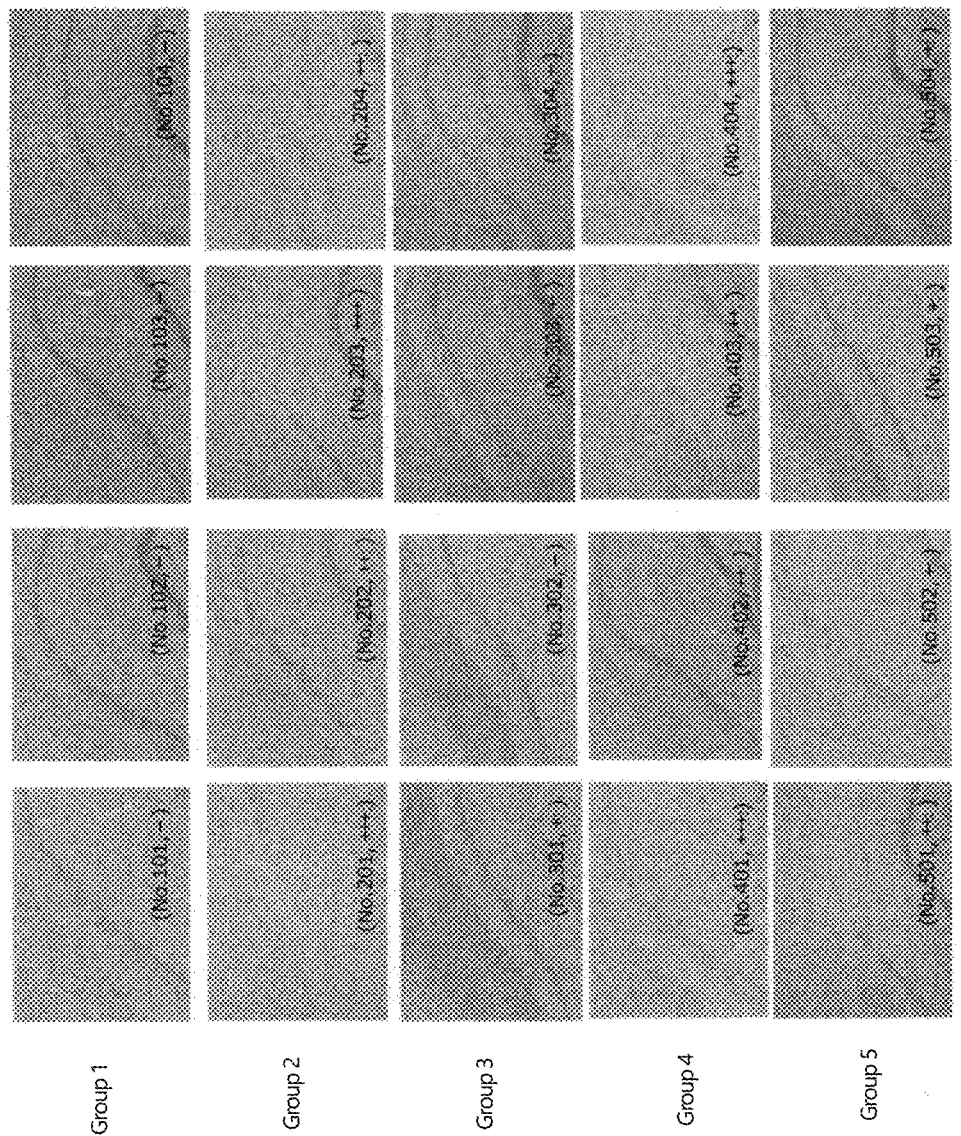
FIG. 3C shows HE staining images of left hippocampus CA1 in each rat.

The improvement effects on spatial learning capacity and spatial memory capacity were also demonstrated by HE-stained pathologic specimens of hippocampal CA1 regions (Table 8 and FIGS. 3A, 3B, 3C). Three to seven days after ischemia, delayed neuronal cell death of hippocampal CA1 pyramidal cells is observed in four-vessel occlusion-reperfusion models (Johansen F. F., et al.: Acta Neuropathologica 61, 135-140, 1983). In the Morris water maze test performed 1 week after ischemia in this experiment, a prolonged time was also taken to reach the platform presumably due to delayed neuronal cell death. Further, as shown in Table 8 and FIGS. 3A, 3B, and 3C, hippocampal CA1 neuronal cell death was observed 28 days after the four-vessel occlusion surgery. The shedding was observed even with administration (treatment) of taltirelin after delayed neuronal death. When both arundic acid and taltirelin were administered, delayed neuronal death was very slightly observed. Although arundic acid promoted regeneration of hippocampal CA1 neuronal cells, it did not affect spatial learning capacity and spatial memory capacity in the Morris water maze test. In contrast, administration of a combination of arundic acid and taltirelin improved spatial learning and memory capacity. It was thus speculated that improvement effects on spatial learning capacity and spatial memory capacity were provided because arundic acid regenerated neuronal cells and taltirelin promoted construction of a neural circuit. The results further suggest that administration of a combination of arundic acid and taltirelin promotes nerve cell regeneration and neural circuit formation. Accordingly, administration of a combination of arundic acid and taltirelin is expected to promote neuronal regeneration and circuit formation, even in other neurodegenerative diseases and cerebral infarction.

TABLE 8

| Group | One group (number of rats) | 4-VO | Animal number | Occurrence/non-occurrence of CA1 shedding, and degree of neuronal death | |
|---|---|---|---|---|---|
| | | | | Left | Right |
| 1 | 6 | − | 101 | − | − |
| | | | 102 | − | − |
| | | | 103 | − | − |
| | | | 104 | − | − |
| | | | 105 | − | − |
| | | | 106 | − | − |
| 2 | 4 | + | 201 | +++ | +++ |
| | | | 202 | ++ | ++ |
| | | | 203 | +++ | +++ |
| | | | 204 | ++ | +++ |
| 3 | 4 | + | 301 | + | + |
| | | | 302 | − | − |
| | | | 303 | + | + |
| | | | 304 | − | − |
| 4 | 4 | + | 401 | +++ | +++ |
| | | | 402 | ++ | ++ |
| | | | 403 | ++ | ++ |
| | | | 404 | +++ | +++ |
| 5 | 4 | + | 501 | ++ | + |
| | | | 502 | + | ++ |
| | | | 503 | + | + |
| | | | 504 | + | ++ |

− No Neuronal cell death,
+ Neuronal cell loss (slight),
++ Neuronal cell death (moderate),
+++ Neuronal cell death (severe)

Further, a combination of arundic acid and taltirelin achieved the above effects, even though their dose was about ⅓ that of arundic acid or taltirelin used alone. Accordingly, a combination of arundic acid and taltirelin is expected to provide the above effects, while reducing the side effects of arundic acid and taltirelin. Further, arundic acid has a unique bitter taste. Since a combination of arundic acid and taltirelin can reduce the dose of arundic acid, discomfort during administration is also expected to be reduced.

II. Example 2

Arundic acid salts were produced according to the following method.

1. Synthesis Example 1 (Calcium Chloride Method)

1000 μL (1.0 mmol) of 1N sodium hydroxide was added to 100 μL (90.8 mg, 0.487 mmol, d=0.908) of arundic acid to dissolve the arundic acid, thus obtaining a colorless clear solution. 100 μL of 1M calcium chloride ($CaCl_2$) was added to this solution to form a white turbid mass. The white turbid mass was ultrasonicated and further dispersed. Water was evaporated to dry the white turbid mass to a solid, thus obtaining a solid.

The obtained compound was subjected to FT-IR, thermal analysis, and elemental analysis. The FT-IR was determined by the ATR method using an FT-IR device (Nicolet iS5 FT-IR, produced by Thermo Fisher Scientific) equipped with an ATR attachment (iD5ATR). The measurement was entrusted to Osaka Shinyaku Co., Ltd. The thermal analysis was performed using a TGIDTA device (Thermo plus EV02 TG8121, produced by Rigaku Corporation) and a DSC device (Thermo plus EV02 DSC8231, produced by Rigaku Corporation). Using sample containers made of aluminum, TG-DTA and DSC were measured in a nitrogen stream at a flow rate of 200 ml/min and at a flow rate of 50 ml/min, respectively, both at a temperature rise rate of 50° C./min. The DSC was measured with an aluminum lid being placed on the container, without crimping. With respect to tests for elemental analysis, quantitative analysis using a CHN coder was entrusted to Sumika Chemical Analysis Service, Ltd., and quantitative analysis of Na and Ca by ICP emission spectrometry was entrusted to the Kyoto Prefectural Technology Center for Small and Medium Enterprises.

Figure 4A:
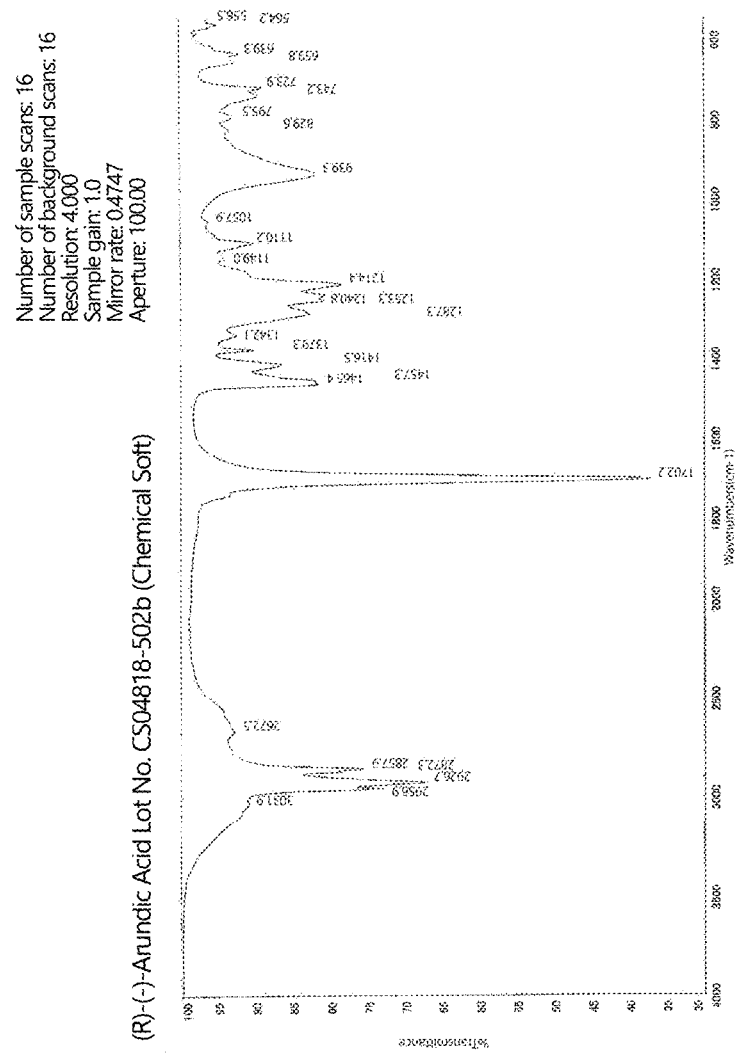
FIG. 4A is a diagram showing NMR results of (R)-arundic acid.
Figure 4B:
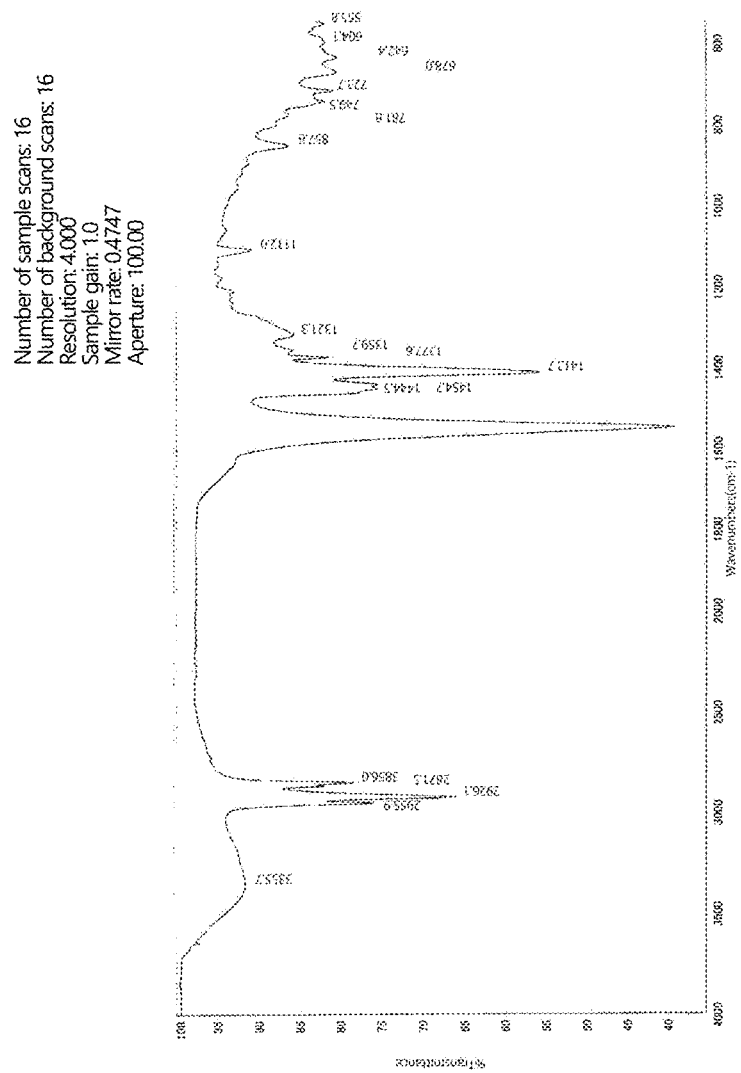
FIG. 4B is a diagram showing NMR results of arundic acid calcium salt synthesized by the calcium chloride method.
Figure 5:
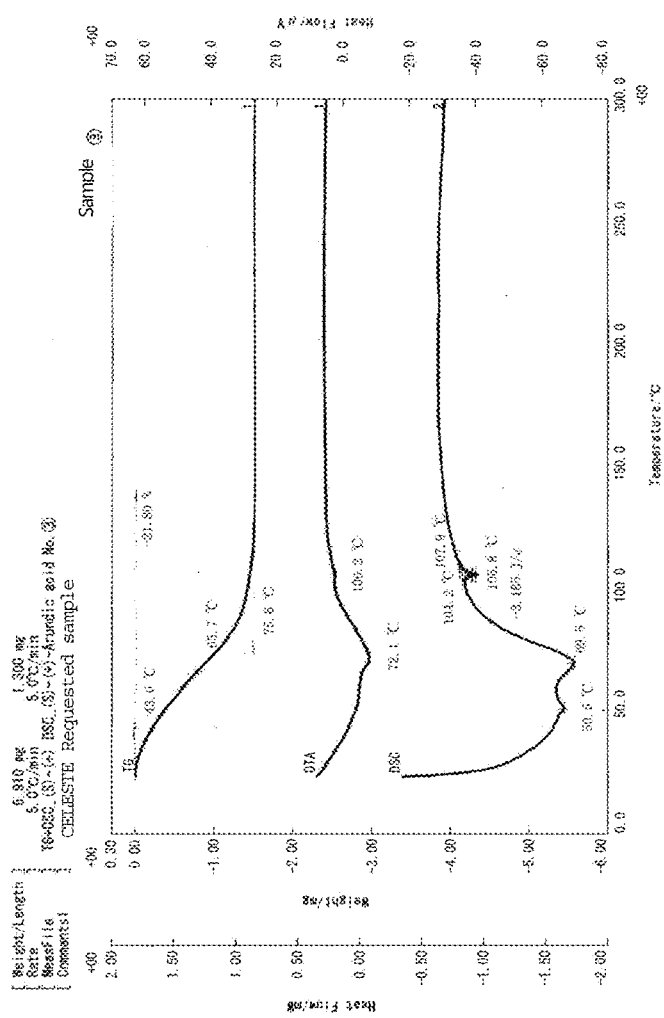
FIG. 5 is a diagram showing thermal analysis results of arundic acid calcium salt synthesized by the calcium chloride method.

FIG. 4A shows FT-IR results of arundic acid, and FIG. 4B shows FT-IR results of the obtained compound. FIG. 5 shows the results of thermal analyses (thermogravimetry TG, differential thermal analysis DTA, and differential scanning calorimetry DSC) of the obtained compound.

The elemental analysis results indicate that C: 48.5%, H: 7.8%, N: <0.3, Na: 19.5, and Ca: 4.77.

2. Synthesis Example 2 (Calcium Carbonate Method)

Arundic acid was dissolved in a lower alcohol (such as methanol or ethanol), and calcium carbonate ($Ca(CO_3)_2$) was added in an equivalent amount to this solution. The precipitated calcium salt was separated by filtration, and washed with alcohol. The precipitated calcium salt was dissolved again in purified water. After the purified water was evaporated, the resulting calcium salt was washed with alcohol to obtain a recrystallized product.

3. Synthesis Example 3 (Ammonia Method)

1000 μL (1.0 mmol) of 1N sodium hydroxide was added to 100 μL of arundic acid (90.8 mg, 0.487 mmol, d=0.908) to dissolve the arundic acid, thus obtaining a colorless clear solution. After 100 μL of ammonia ($NH_3$) water was added to this solution, water was evaporated to obtain a solid. The obtained solid was subjected to FT-IR, thermal analysis, and elemental analysis in the same manner as in Synthesis Example 1.

III. Example 3

A arundic acid calcium salt was synthesized by the following method. In this Example, the unit 1 e.q. (equivalent) refers to the amount of a base (mol) with which 1 mol of the carboxyl group of arundic acid can be just neutralized.

1. Reagents

To synthesize the arundic acid calcium salt in this section, the reagents shown in Table 9 were used.

TABLE 9

| Reagent name | Grade | Manufacturer | Lot No. |
|---|---|---|---|
| Arundic acid | | Soft Chemical Co., Ltd. | CS04818-503 |
| Calcium hydroxide (Ca(OH)$_2$) | AR | Sinopharm Chemical Reagent | F20070126 |
| Calcium chloride (CaCl$_2$) | AR | Shanghai Experiment Reagent | 20150107 |
| Sodium hydroxide | AR | Shanghai Experiment Reagent | 20150111 |
| Methanol | HPLC | Merck | 10886807715 |
| Ethanol | HPLC | J. T. Baker | 0000155943 |
| Acetone | AR | CINC Technologies (Shanghai) | 07306090 |
| Methyl tert-butyl ether (MtBE) | AR | CINC Technologies (Shanghai) | 15307010 |
| Acetonitrile (ACN) | HPLC | Merck | TA055230 |
| Tetrahydrofuran (THF) | HPLC | MACRON | 1612529801 |
| Dichloromethane (DCM) | HPLC | ANPEL Laboratory Technologies (Shanghai) Inc. | 4012001.4000 |
| Heptane | AR | Shanghai Experiment Reagent | 2000144 |
| Ethyl acetate (EA) | AR | CINC Technologies (Shanghai) | 093070101 |
| 2-Propanol (IPA) | HPLC | Sigma-Aldrich | WXBC5107V |
| Methyl ethyl ketone (MEK) | AR | Sinopharm | 1800228187 |
| 34805-HYDRANAL-Composite 5 | KF titration reagent | Honeywell | SZBG2980H |

2. Analysis Method

The analysis of each synthesized compound was performed using the following devices and analysis conditions.

2-1. Powder X-Ray Diffraction (XRPD)

A X-ray powder diffractometer (D8 Advance, Bruker) was used for XRPD. The analysis conditions are as follows.
Tube: Cu K-alpha ($\lambda$=1.54179 Å).
Generator: Voltage: 40 kV; Current: 40 mA.
Scan range: 3 to 40 deg.
Sample rotation speed: 15 r.p.m.
Scan speed: 10 deg./min 2-2. Differential Scanning Calorimetry (DSC)

A differential scanning calorimeter (Q2000, TA Instruments) was used for DSC. Samples (up to 1 mg) were placed in hermetic aluminum pans with pinholes, and heated from 25° C. to 300° C. at a temperature rise rate of 10° C./min.

2-3. Thermogravimetry (TGA)

A thermogravimetric analyzer (Q5000IR, TA Instruments) was used for TGA. Samples (3 to 5 mg) were placed in openable hermetic platinum pans, and heated at a temperature rise rate of 10° C./min in the presence of N$_2$ (25 mL/min) from 30° C. to 300° C.; or heated at a temperature rise rate of 10° C./min in the presence of N$_2$ (25 mL/min) until the weight of each sample was reduced to 80% by weight of the sample originally fed.

2-4. $^1$H NMR Analysis $^1$H NMR analysis was performed according to the following method using a $^1$H proton nuclear magnetic resonance spectrometer (UltraShield, Bruker). A sample (10 mg) was dissolved in 1.0 mL methanol-d4 (MeOD), and this sample was analyzed at a magnetic field intensity of 400 MHz.

2-5. Polarizing Microscope (PLM)

An LV100 PL (Nikon) equipped with a 5-megapixel CCD was used as a polarizing microscope.

2-6. High-Performance Liquid Chromatography (HPLC)

HPLC was performed using an Agilent 1260 (Agilent). Table 10 shows the conditions.

TABLE 10

| Device | High-Performance Liquid Chromatograph |
|---|---|
| Column details | Eclipse Plus C18 3.5 um_959961-902 |
| Column temperature | 25° C. |
| Movable phase A | 0.1% FA in water |
| Mobile phase B | Acetonitrile |
| Flow rate | 1 mL/min |

| | Time (mins) | % Mobile Phase A | % Mobile Phase B |
|---|---|---|---|
| Gradient profile | 0.00 | 95 | 5 |
| | 15.00 | 5 | 95 |
| | 15.10 | 95 | 5 |
| | 20.00 | 95 | 5 |

| Flow rate | 1.0 mL/min |
|---|---|
| Detection wavelength | 210 nm |
| Injection volume | 10 μL |
| Dilution | Methanol |

2-7. Compound Structure Estimation

The structure of the compound was estimated from the molecular structure information on arundic acid (R-(−) arundic acid) and calcium ion (Ca$^{2+}$). Estimation of characteristics and confirmation of stoichiometry were performed based on the ICP-OES analysis values, the KF titration results, and the NMR results described below.

2-8. Inductively Coupled Plasma Atomic Emission Spectrometry (ICP-OES)

100 mg of each sample was dissolved in a mixture of 6 mL of hydrochloric acid and 2 mL of nitric acid under microwave irradiation, and analyzed using an inductively coupled plasma optical emission spectrometer (700 Series, Agilent) under the following conditions.

Transmit power: 1.3 KV.
Carrier gas: Ar.
Plasma gas flow: 15 L/min.
Auxiliary gas flow: 1.5 L/min.
Atomizer pressure: 220 KPa.
Detection mode: axial observation.
Calibration type: linear.

2-9. Carl Fischer (KF) Titration

After methanol was placed as a solvent into a volume KF volumetric Karl Fischer titration device (V20, Mettler-Toledo), 100 mg of a sample was placed and titrated to an endpoint using HYDRANAL-Composite 5.

3. Reference Synthesis Examples 1 to 7

102 μL (100 mg) of arundic acid was dissolved in 500 μl of ethanol, acetone, or methanol. Then, 50 μL of an aqueous solution of 22.1 mg of $Ca(OH)_2$, 0.35 g/mL $CaCl_2(OH)_2$, or 0.54 g/mL NaOH was added thereto (Reference Synthesis Example 1: a combination of ethanol and $CaCl_2$, Reference Synthesis Example 1: a combination of ethanol and $Ca(OH)_2$, Reference Synthesis Example 3: a combination of acetone and $CaCl_2$, Reference Synthesis Example 4: a combination of acetone and $Ca(OH)_2$, Reference Synthesis Example 5: a combination of methanol and $CaCl_2$, Reference Synthesis Example 6: a combination of methanol and $Ca(OH)_2$, and Reference Synthesis Example 7: a combination of methanol and NaOH). The vials after the addition were heated to 50° C., and incubated at 50° C. for 2 hours. No crystals were not obtained in Reference Synthesis Examples 1 to 7 (not shown).

4. Synthesis Examples 4 to 8 and Reference Synthesis Examples 8 to 12

22.12 mg of $Ca(OH)_2$ was placed in each of 2-mL vials, and 102 μL (100 mg) of arundic acid was added to each vial. 500 μL portions of different solvents were individually added to the vials containing $Ca(OH)_2$ and arundic acid. The solvents used were MtBE (Synthesis Example 4), ACN (Synthesis Example 5), THF (Synthesis Example 6), DCM (Synthesis Example 7), and heptane (Synthesis Example 8). The vials after adding the solvents were heated to 50° C., and incubated at 50° C. for 18 hours. The vials were then cooled to 25° C., and incubated at 25° C. for 1 hour. The liquids in the vials after the incubation were suspensions. The suspensions were centrifuged to separate residual solid components and a supernatant. The residual solid components and the supernatant were dried at 30° C. for 3 hours using a vacuum oven. The solid components obtained after drying were analyzed by XRPD.

Table 11 shows the properties of Synthesis Examples 4 to 8.

TABLE 11

| Syn-thesis Example | Base | Solvent | Observation | XRPD Results Solids from suspension | Solids from liquid |
|---|---|---|---|---|---|
| 4 | $Ca(OH)_2$ (0.55 e.q.) | MtBE | Suspension | Pattern C-I | Pattern C-I |
| 5 | | ACN | Oil came out | Pattern C-I | N/A |

TABLE 11-continued

| Syn-thesis Example | Base | Solvent | Observation | XRPD Results Solids from suspension | Solids from liquid |
|---|---|---|---|---|---|
| 6 | | THF | Suspension | Partially amorphous | Partially amorphous |
| 7 | | DCM | Frozen* | Patten C-I | N/A |
| 8 | | Heptane | Suspension | Few $Ca(OH)_2$ + amorphous | Amorphous |

*Since this system was frozen and failed to separate residual solid components and a supernatant, the entire reaction mixture was placed in an oven and dried.

Figure 6:
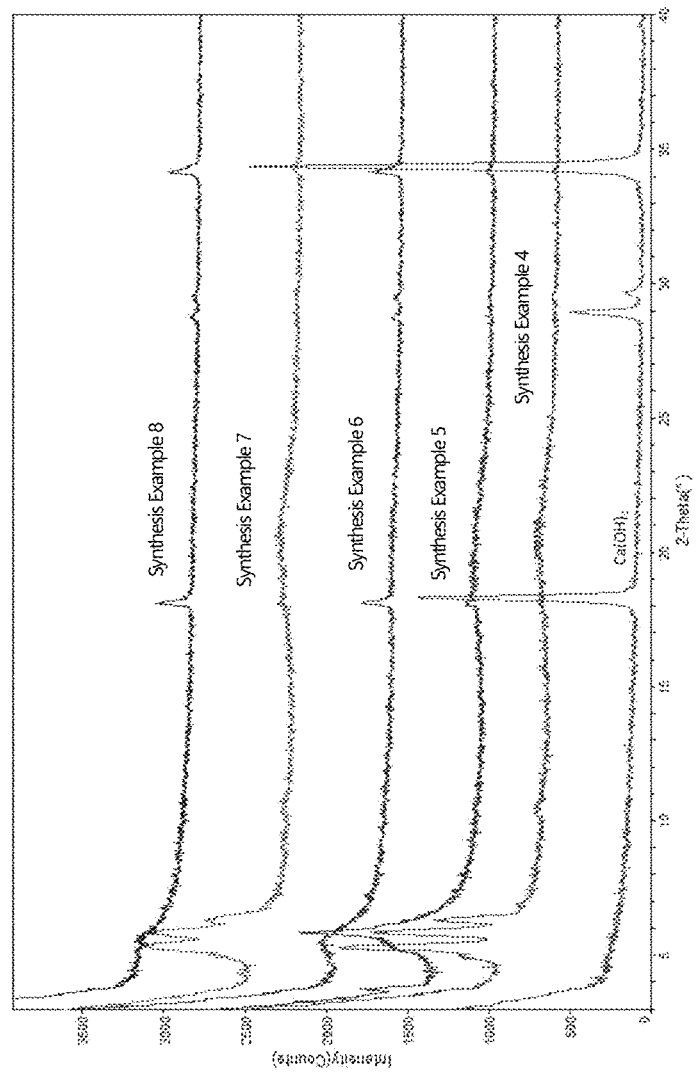
FIG. 6 shows XRPD analysis results of residual solid components obtained in Synthesis Examples 4 to 8.
Figure 7:
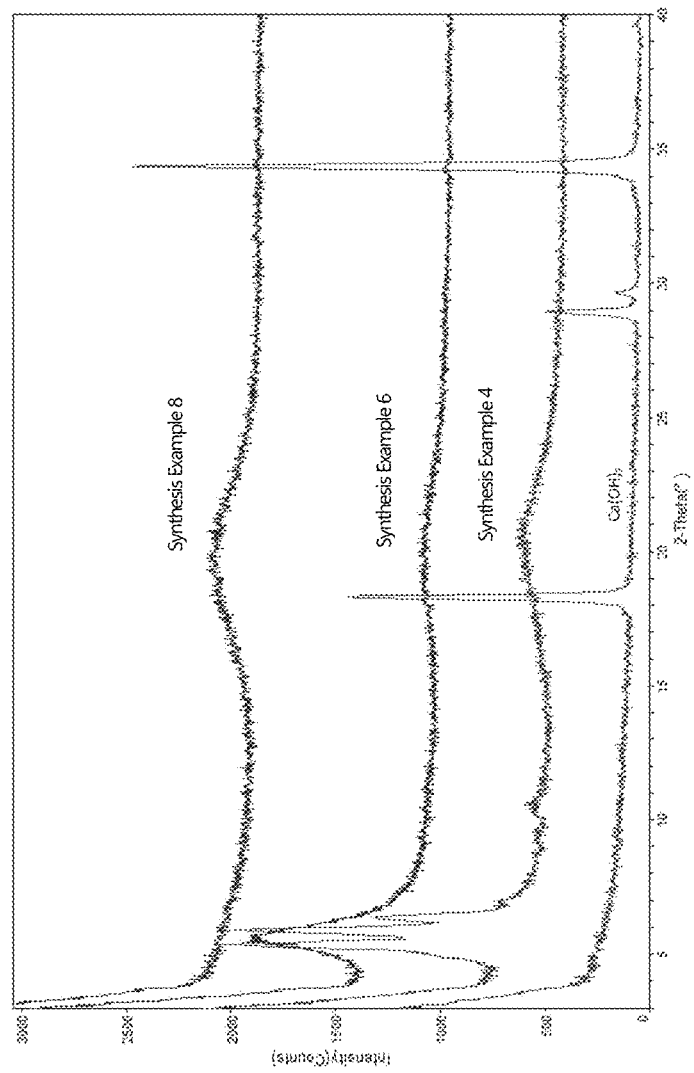
FIG. 7 shows XRPD analysis results of solid components obtained from supernatants of Synthesis Examples 4, 6, and 8.

FIGS. 6 and 7 show the XRPD analysis results of each solid component. In XRPD analysis, a new peak pattern (referred to as "pattern C-I") was confirmed at approximately 2θ (2-theta)=5° to 7°. The results suggest that a solid component, which is presumably an arundic acid calcium salt, was present in the residue solid components of Synthesis Examples 4 to 8 (FIG. 6). An arundic acid calcium salt was considered to be also present in the solid components obtained from supernatants of Synthesis Examples 4, 6, and 8 (FIG. 7).

Subsequently, synthesis of an arundic acid calcium salt using $CaCl_2$ in place of $Ca(OH)_2$ was attempted using the same protocol as $Ca(OH)_2$ (Reference Synthesis Example 8 (MtBE), Reference Synthesis Example 9 (ACN), Reference Synthesis Example 10 (THF), Reference Synthesis Example 11 (DCM), and Reference Synthesis Example 12 (heptane)). However, when $CaCl_2$ was used, no new peak was observed in XRPD analysis (not shown).

5. Synthesis Example 9 and Reference Synthesis Example 13

Subsequently, a sodium salt of arundic acid was prepared, and a method for preparing an arundic acid calcium salt from an arundic acid sodium salt was attempted.

5-1. Reference Synthesis Example 13

102 μL (100 mg) of arundic acid was dissolved in 500 μL of acetone, and 50 μL of a 0.54 g/mL NaOH aqueous solution was added to this solution. The resulting solution was heated to 50° C., and incubated at 50° C. for 2 hours. A 0.35 mg/mL $CaCl_2$ aqueous solution (100 μL) was added to the solution after incubation. An oily component appeared upon this reaction. After 400 μL of water was further added thereto, the resulting mixture was incubated at 50° C. for 2 hours, then cooled to 25° C., and incubated at 25° C. for 20 hours. The oily component remained unchanged, and did not solidify.

5-2. Synthesis Example 9

102 μL (100 mg) of arundic acid was dissolved in 500 μL of THF, and 50 μL of a 0.54 g/mL NaOH aqueous solution was added to this solution. The resulting solution was heated to 50° C. and incubated at 50° C. for 4 hours. The solution after incubation was then cooled to 25° C. and incubated at 25° C. for 20 hours. 100 μL of a 0.35 mg/mL $CaCl_2$ aqueous solution was added to the solution after incubation. A suspension was obtained by this reaction. This suspension was heated to 50° C., incubated at 50° C. for 2 hours, and then cooled to 25° C. The resulting suspension was centrifuged to separate residual solid components and a supernatant (mother liquor). The mother liquor was dried in a 30° C. vacuum oven for 17 hours, thus obtaining a gel-like solid. The residual solid components of the suspension and the solid components obtained from the mother liquor were analyzed by XRPD.

5-3. Results

Figure 8:
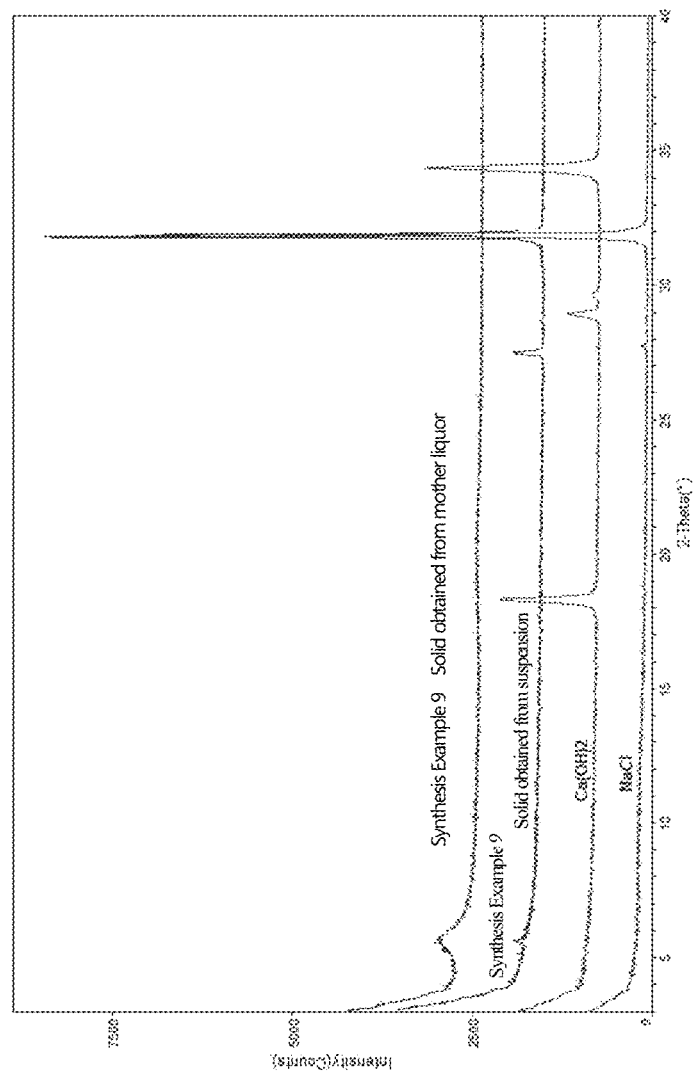
FIG. 8 shows XRPD analysis results of solid components obtained in Synthesis Example 9.

Table 12 shows properties of the compounds obtained in Synthesis Example 9 and Reference Synthesis Example 13. FIG. 8 shows the XRPD results.

TABLE 12

|  | Base | Solvents | Observation | Solids from suspension | Solids from liquid |
|---|---|---|---|---|---|
| Synthesis Example 9 | 1.1 e.q. NaOH + 0.55 e.q. CaCl$_2$ | THF | Suspension | NaCl | Amorphous |
| Reference Synthesis Example 13 | | Acetone:water (1v:1v) | Oil came out | N/A | N/A |

In Synthesis Example 9, an amorphous product was obtained from the mother liquor, and the residual solid component was NaCl. No solid components were obtained in Reference Synthesis Example 13.

6. Synthesis Example 10

By using the system of Synthesis Example 4 as a system for synthesizing an arundic acid calcium salt and using 200 mg of arundic acid, a scale-up was attempted.

44.24 mg of Ca(OH)$_2$ and 204 μL (200 mg) of arundic acid were suspended in 1.0 mL of MtBE. The resulting suspension was heated to 40° C., and incubated at 40° C. for 24 hours. The suspension was then cooled to 25° C. A part of the solid component did not dissolve, and the resulting mixture was highly viscous. The solvent was dried in a vacuum oven to obtain a gel-like solid component. This solid component was dissolved in 2.0 mL of methanol. The solid component that remained undissolved was removed by centrifugation, and a supernatant was collected. The supernatant (mother liquor) was subjected to rotary evaporation in vacuum. The wet residue was dried using a vacuum oven at 30° C. for 65 hours. After the drying, the obtained solid components were subjected to 1H NMR, XRPD, DSC, TGA, and PLM analyses.

Table 13 shows properties of the compound obtained in Synthesis Example 10. FIGS. 9 to 12 show the results of $^1$H NMR, XRPD, DSC, TGA, and PLM.

Figure 9:
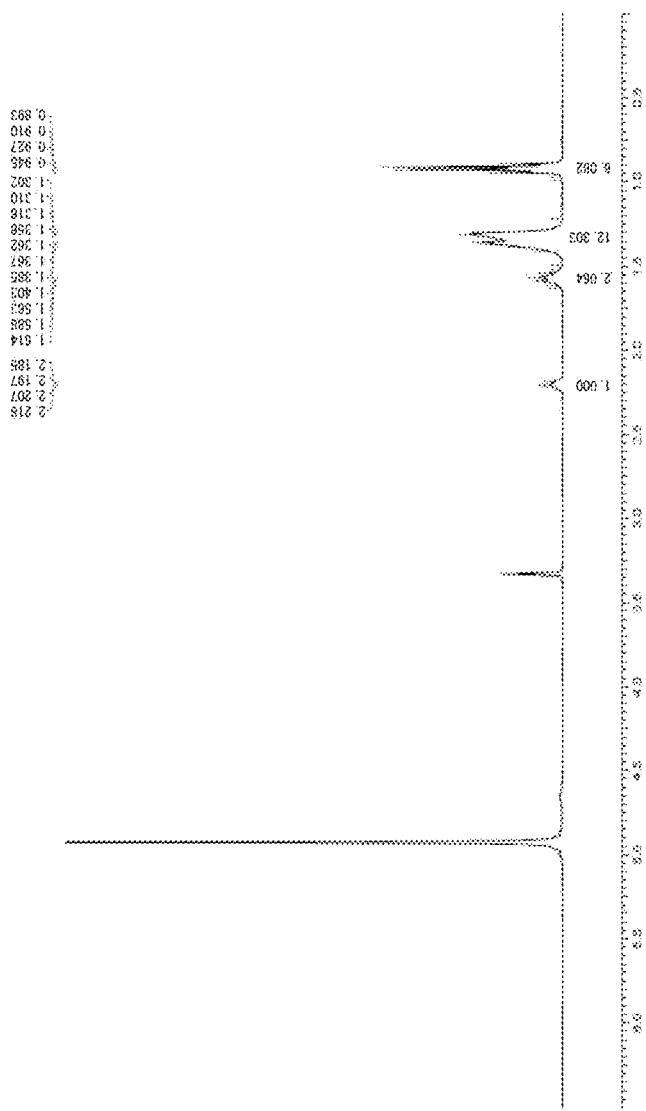
FIG. 9 shows $^1$H NMR results of a solid component obtained from mother liquor in Synthesis Example 10.
Figure 10:
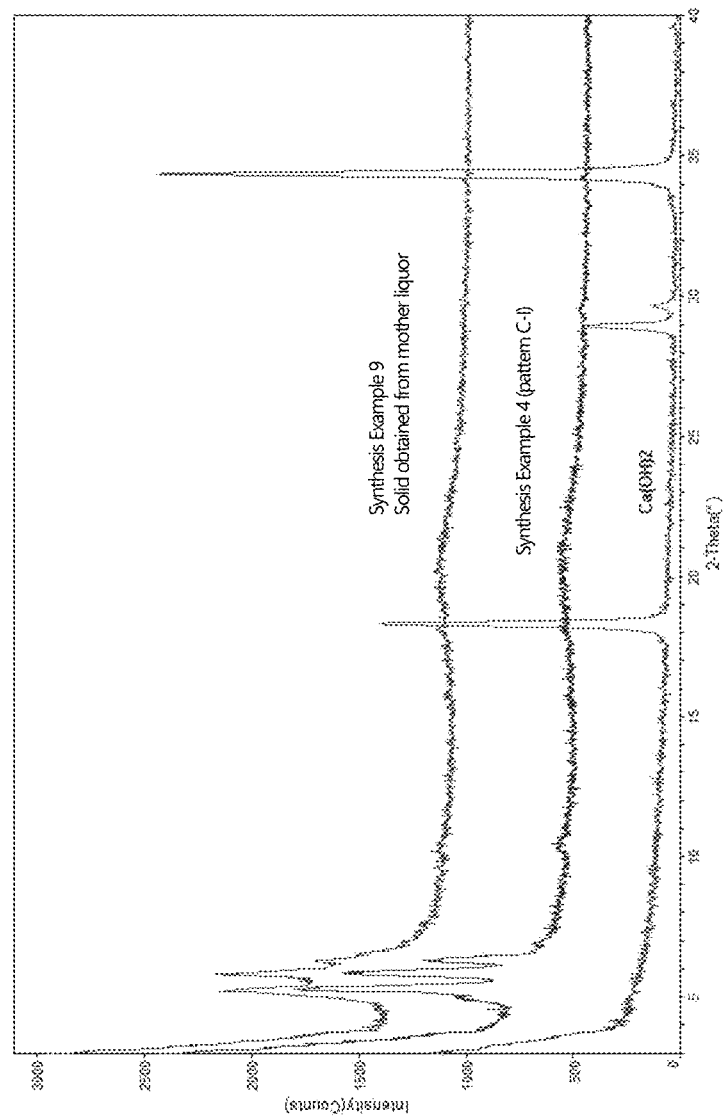
FIG. 10 shows XRPD analysis results of the solid component obtained from the mother liquor in Synthesis Example 10.
Figure 11:
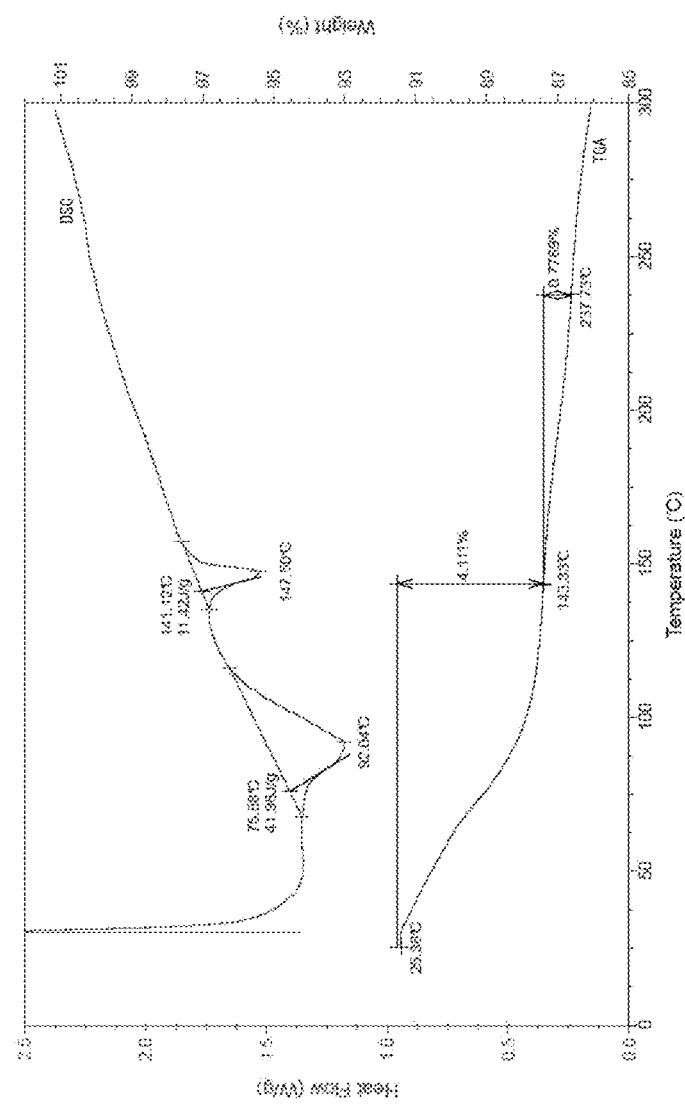
FIG. 11 shows results of DSC analysis and TGA analysis of the solid component obtained from the mother liquor in Synthesis Example 10.
Figure 12:
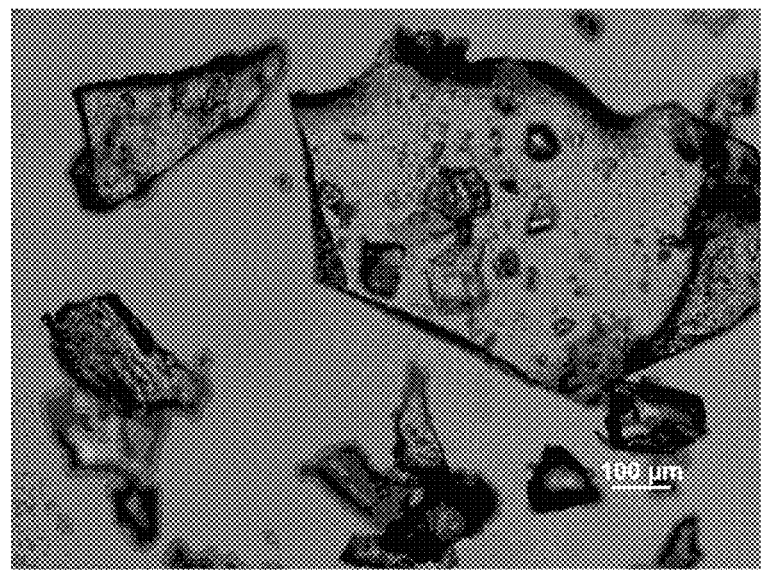
FIG. 12 shows a polarizing microscopy image of the solid component obtained from the mother liquor in Synthesis Example 10.

$^1$H NMR shows that the total number of hydrogen atoms of the solid component obtained from the mother liquor in Synthesis Example 10 was in agreement with the theoretical value. The residual MtBE or methanol was not observed (FIG. 9). In XRPD, the solid component obtained from the mother liquor in Synthesis Example 10 showed the same peak pattern C-I as Synthesis Example 4 (FIG. 10). In the DSC scan (FIG. 11) of Synthesis Example 10, one endothermic peak appeared at 92.04° C., and another endotherm subsequently appeared at 147.50° C. The TGA scan showed a weight loss of 4.11% from 25.4° C. to 143.3° C., and a weight loss of 0.78% from 143.3° C. to 237.7° C. The polarizing microscope observation confirmed the presence of crystals (FIG. 12).

7. Synthesis Example 11

Subsequently, a scale-up of the system of Synthesis Example 9 was attempted using 500 mg of arundic acid.

510 μL (500 mg) of arundic acid was dissolved in 500 μL of THF, and 250 μL of a 0.54 g/mL NaOH aqueous solution was added to this solution. The resulting solution was heated to 50° C., and incubated at 50° C. for 3 hours. The solution became transparent. 500 μL of a 0.33 g/mL CaCl$_2$ aqueous solution was then added to the solution after incubation. A suspension was obtained by this reaction. The suspension was maintained at 50° C. for 3 hours, then cooled to 25° C., and incubated at 25° C. for 30 minutes. The suspension was centrifuged to separate residual solid components and a supernatant (mother liquor). The residual solid components were washed with 2.0 ml of THF. The mother liquor was subjected to rotary evaporation in vacuum, and the solvent was removed. The wet residue was dried at 30° C. for 65 hours using a vacuum oven. After the drying, the obtained solid components were subjected to $^1$H NMR, XRPD, DSC, TGA, and PLM analyses. The residual solid components were analyzed by XRPD.

TABLE 13

|  | Base | Solvents | Observation | Solids from suspension* | Solids from liquid |
|---|---|---|---|---|---|
| Synthesis Example 10 | 0.55 e.q. Ca(OH)$_2$ | MtBE | Suspension | N/A | Pattern C-I |

Table 14 shows properties of the compound obtained in Synthesis Example 11. FIGS. 13 to 16 show the results of $^1$H NMR, XRPD, DSC, TGA, and PLM.

TABLE 14

| | | | | XRPD Results | |
|---|---|---|---|---|---|
| | Base | Solvents | Observation | Solids from suspension | Solids from liquid |
| Synthesis Example 11 | 1.1 e.q. NaOH + 0.55 e.q. CaCl$_2$ | THF | Suspension | NaCl | Amorphous |

Figure 13:
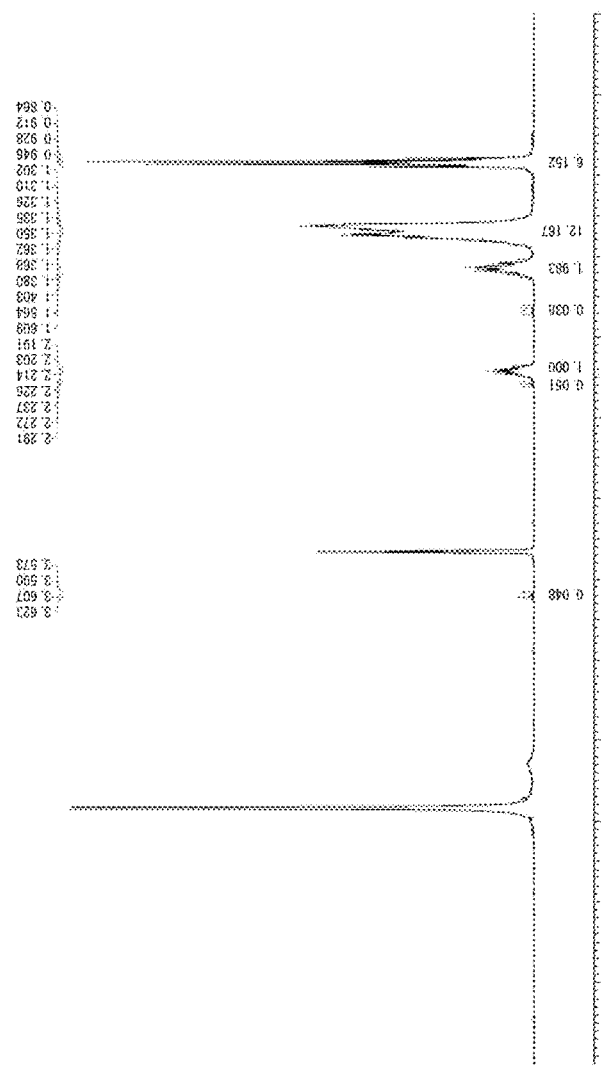
FIG. 13 shows $^1$H NMR results of a solid component obtained from mother liquor in Synthesis Example 11.
Figure 14:
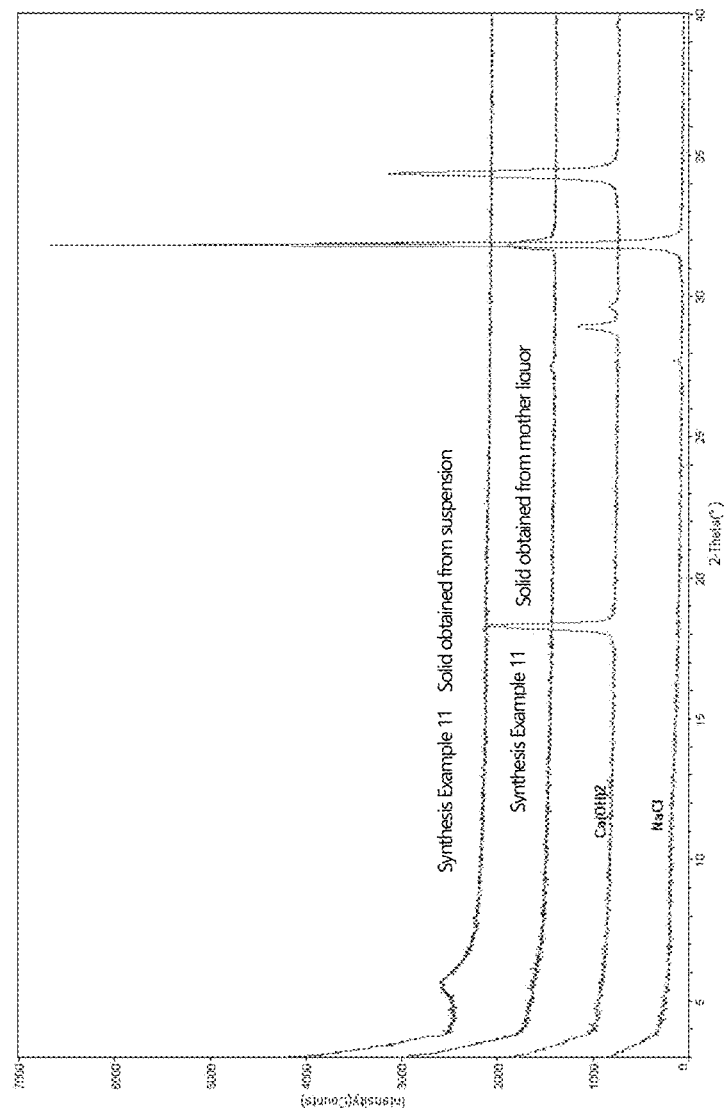
FIG. 14 shows XRPD analysis results of the solid component obtained from the mother liquor and a solid component obtained from a suspension in Synthesis Example 11.
Figure 15:
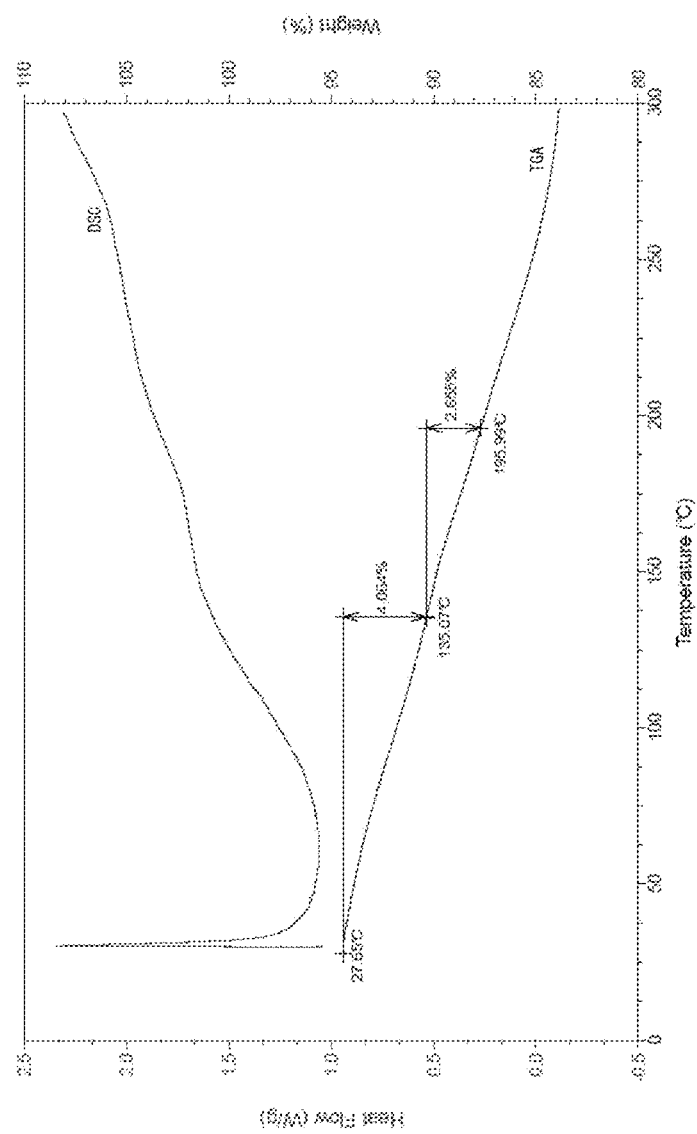
FIG. 15 shows results of DSC analysis and TGA analysis of the solid component obtained from the mother liquor in Synthesis Example 11.
Figure 16:
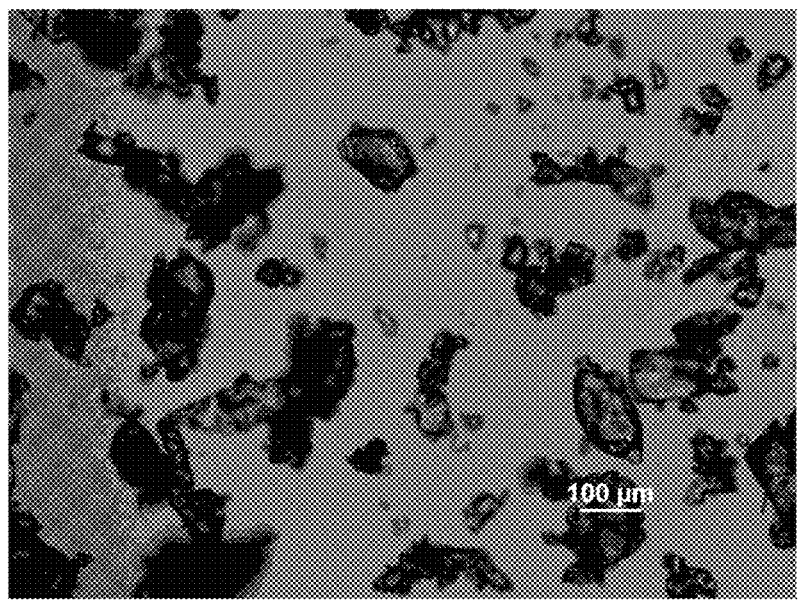
FIG. 16 shows a polarizing microscopy image of the solid component obtained from the mother liquor in Synthesis Example 11.

$^1$H NMR shows that the number of hydrogen atoms in the solid component obtained from the mother liquor in Synthesis Example 11 was in agreement with the theoretical value. However, about 0.38% of THF remained (FIG. 13). XRPD shows that the residual solid component of the suspension obtained in Synthesis Example 11 was NaCl (FIG. 14). The solid component obtained from the mother liquor in Synthesis Example 11 had an amorphous structure (FIG. 14). In the DSC scan (FIG. 15) of the amorphous solid obtained in Synthesis Example 11, the TGA scan showed a weight loss of 4.06% from 27.6° C. to 135.1° C., and a weight loss of 2.65% from 135.1° C. to 196.0° C. The polarizing microscope observation confirmed the presence of crystals (FIG. 16).

8. Synthesis Example 12

The system of Synthesis Example 4 was simple as a method for synthesizing an arundic acid calcium salt, and was able to produce a high-purity compound. Accordingly, using this system, synthesis of an arundic acid calcium salt from 6 g of arundic acid was attempted.

1.33 g of Ca(OH)$_2$ and 6120 μl (6 g) of arundic acid were suspended in 30 mL of MtBE. The suspension was heated to 50° C., incubated at 50° C. for 21 hours, and then cooled to 25° C. Some solid components did not dissolve, and the suspension remained opaque. The suspension was centrifuged at 8000 r.p.m. for 5 minutes. Insoluble solid components were removed, and the supernatant (mother liquor) was collected. The solvent of the mother liquor was removed by rotary evaporation. The obtained wet residue was dried at 30° C. for 2 hours using a vacuum oven. After the drying, the obtained solid components (hereinafter referred to as "Compound of Synthesis Example 12") were subjected to $^1$H NMR, XRPD, DSC, TGA, PLM, logical structure, purity, and solubility analyses. The calcium content of the solid components was measured by inductively coupled plasma atomic emission spectrometry (ICP-OES). Further, the water content was measured by Carl Fischer (KF) titration.

Table 15 shows properties of the compound obtained in Synthesis Example 12. Table 16 shows the purity. Table 17 shows the solubility. FIGS. 17 to 22 show the results of $^1$H NMR, XRPD, DSC, TGA, PLM, logical structure, and HPLC.

TABLE 15

| | Observation | XRPD Results | Calcium content (measured by ICP-OES) | Theoretical calcium content | Water content (KF) |
|---|---|---|---|---|---|
| Synthesis Example 12 | Suspension | Pattern C-I | 10.34% | 9.76% | 5.03% |

Figure 17:
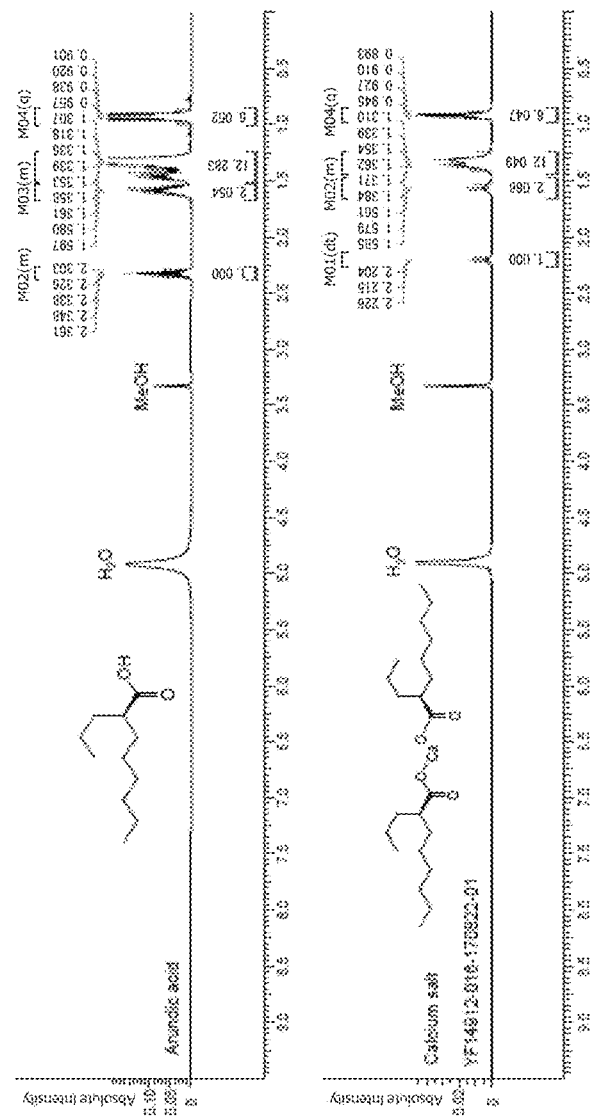
FIG. 17 shows $^1$H NMR results of Compound of Synthesis Example 12.
Figure 18:
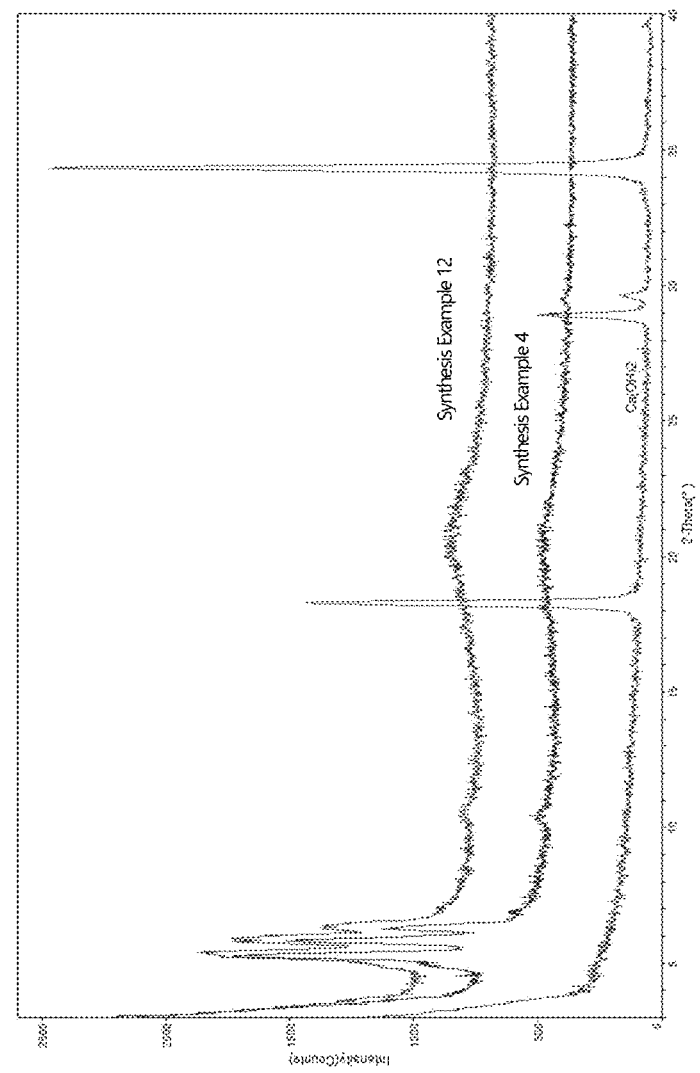
FIG. 18 shows XRPD analysis results of Compound of Synthesis Example 12.
Figure 19:
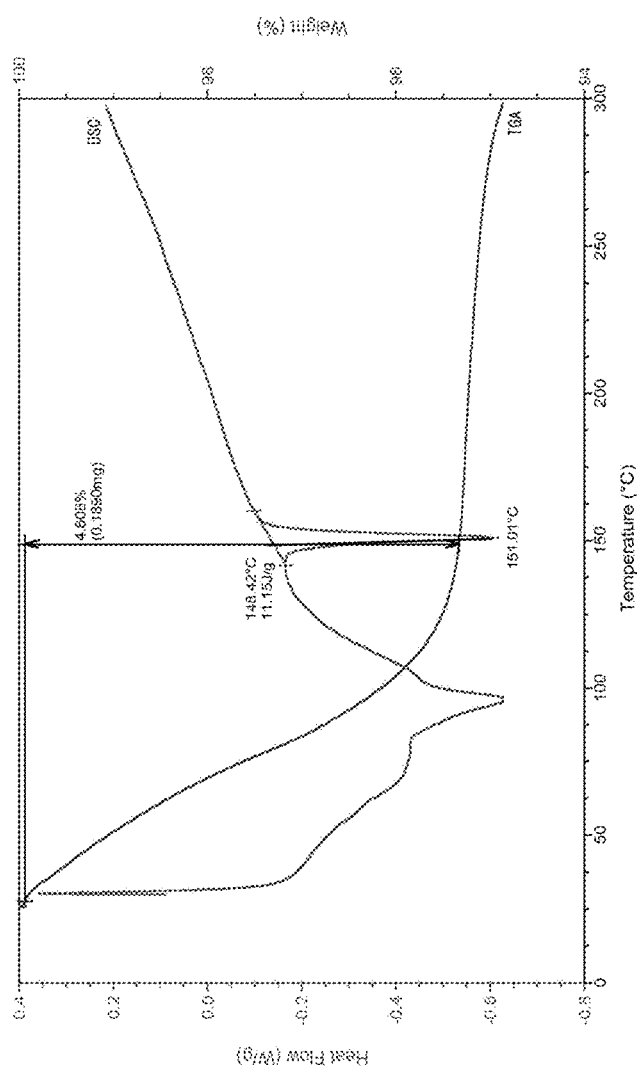
FIG. 19 shows results of DSC analysis and TGA analysis of Compound of Synthesis Example 12.
Figure 20:
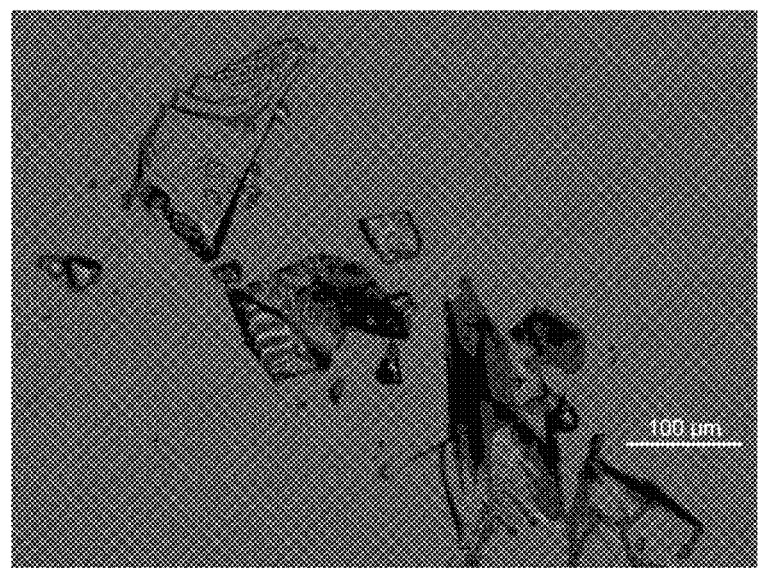
FIG. 20 shows a polarizing microscopy image of Compound of Synthesis Example 12.
Figures 1, 28:
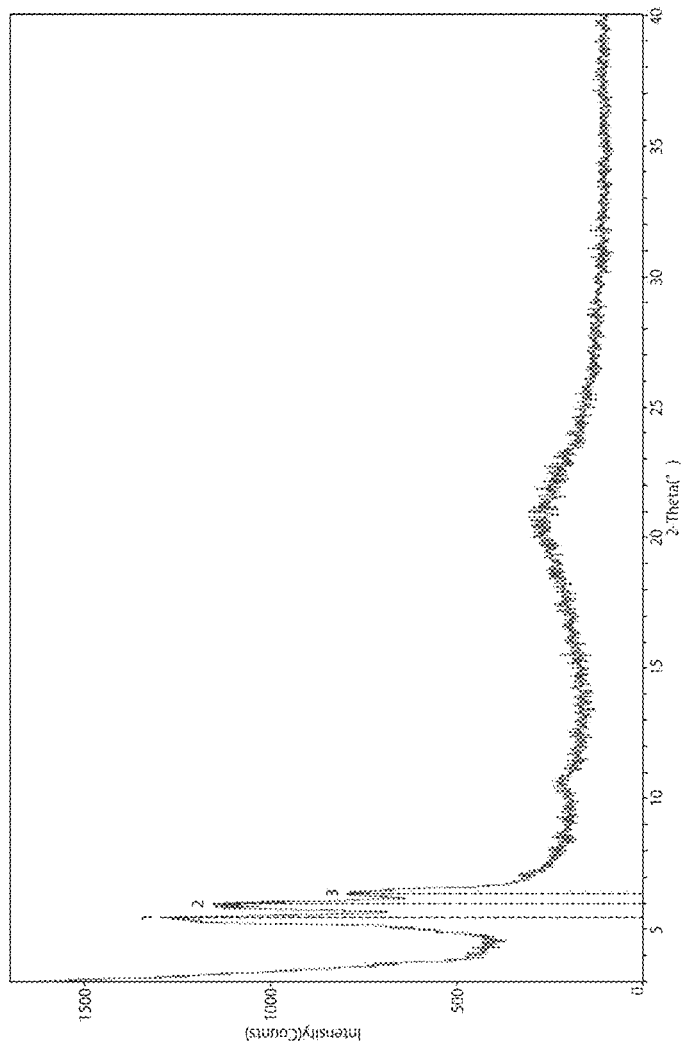

$^1$H NMR shows that the total number of hydrogen atoms in the compound of Synthesis Example 12 was in agreement with the theoretical value. No residual MtBE was observed (FIG. 17). The XRPD analysis shows that the peak pattern of the compound of Synthesis Example 12 was pattern C-I (FIG. 18). FIG. 28 is a table in which peaks in XRPD of the compound of Synthesis Example 12 were quantified. In the DSC scan (FIG. 19) of the compound of Synthesis Example 12, one endothermic peak appeared at 151.1° C. The TGA scan shows a weight loss of 4.6% from 35° C. to 150° C. The polarizing microscope observation shows that the compound of Synthesis Example 12 was amorphous (FIG. 20). The compound of Synthesis Example 12 had a calcium content of 10.34% (Table 15). The arundic acid content of the solid components was 83.85%, and the ratio of arundic acid to calcium was 1:0.57. The water content was about 5.03% (Table 15). This result suggests that a trace of water remained in the synthesized arundic acid calcium salt.

Figure 21:
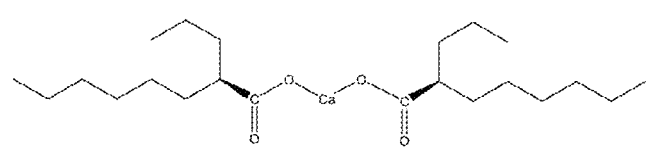
FIG. 21 shows a logic structural formula of Compound of Synthesis Example 12.
Figure 22:
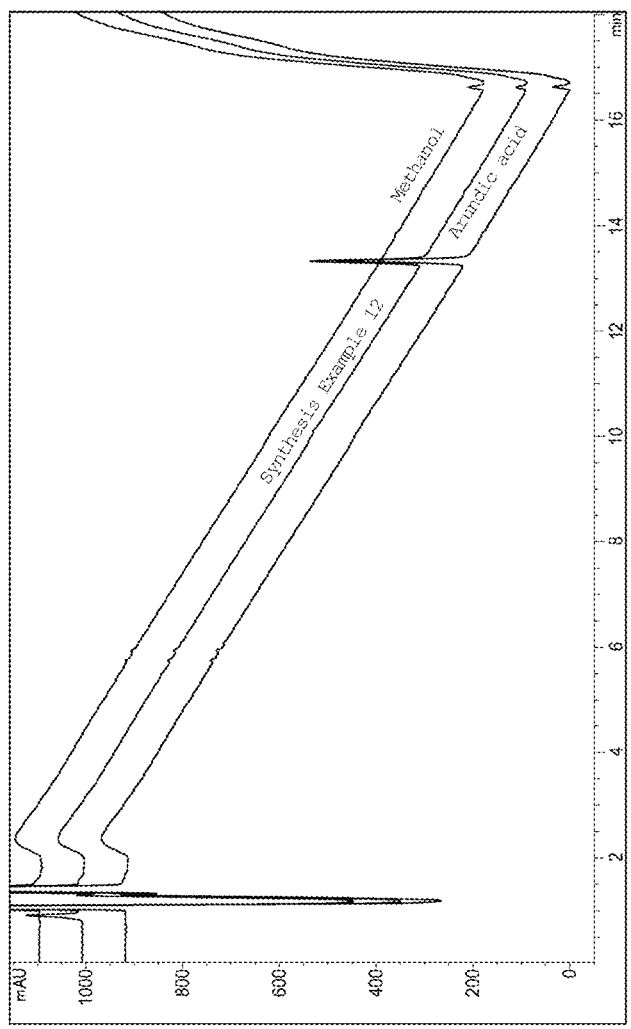
FIG. 22 shows HPLC analysis results of Compound of Synthesis Example 12.

Based on the theoretical structure of the calcium salt shown in FIG. 21 (calcium (R)-2-propyloctanoate (S)-2-propyloctanoate, chemical formula: C$_{22}$H$_{42}$CaO$_4$, molecular weight: 410.64, elemental analysis: C, 64.35; H, 10.31; Ca, 9.76), the theoretical calcium content was calculated to be 9.76%.

The purity was analyzed by HPLC. 100 mg of arundic acid and 100 mg of the compound of Synthesis Example 12 were individually dissolved in 20 mL of methanol at 25° C., and subjected to HPLC analysis. The solid component from the mother liquor of Synthesis Example 12 had a purity of 99.54%, and no contamination by impurities was observed (Table 16, FIG. 22).

TABLE 16

| Item | Lot no. | Purity | Calculated content of arundic acid | Calcium content (ICP-OES) | Acid:calcium ratio |
|---|---|---|---|---|---|
| Arundic acid | CS04818-503 | 99.54% | N/A | N/A | N/A |
| Calcium salt | Compound of Synthesis Example 12 | 99.54% | 83.85% | 10.34% | 1:0.57 |

The approximate solubility of the calcium salt in different solvents at 25° C. was tested by manual dilutions in combination with visual observation. Table 17 shows the results. The compound of Synthesis Example 12, which is poorly soluble in water, dissolved in ethanol, 2-propanol, MtBE, EA, and THF.

TABLE 17

| Solvents | Solubility at 25° C. S (mg/ml) |
|---|---|
| Methanol | N/A* |
| Ethanol | S > 184.8 |
| 2-Promanol | S > 210.0 |
| EA | S > 198.8 |
| THF | S > 198.0 |
| CAN | S < 1.5 |
| MEK | 94.4 < S < 188.8 |
| MtBE | S > 215.2 |
| Acetone | S < 1.7 |
| Water | S < 1.0 |

*The resulting mixture was always opaque, and it was impossible to determine the concentration at which the resulting mixture became transparent.

9. Recrystallization Screening 9-1. Recrystallization by the Slurry Method or the Evaporation Method The compound of Synthesis Example 12 was recrystallized by the slurry method or the evaporation method. Table 18 shows solvents for recrystallization. 30 mg of the compound of Synthesis Example 12 was suspended in 500 ml of each solvent at 25° C. After stirring for 1 hour, the resulting solution became transparent in systems in which THF, MtBE, ethanol, or 2-propanol was used as a solvent. In these systems, recrystallization by the evaporation method was attempted. In the evaporation method, the solution was in contact with air at 25° C. for 21 hours to evaporate the solvent. In solvent systems in which the resulting solutions did not become transparent, recrystallization was attempted by the slurry method. In the slurry method, the solution was suspended under the conditions shown in Table 18, and then centrifuged at 8,000 r.p.m. for 5 minutes to remove the solvent. The residual solid components were then dried at 20° C. for 2.5 hours using a vacuum oven.

Table 18 shows the results.

TABLE 18

| Batch No. | Solvent | Temp. | Time | Method | Observation | Crystalline form |
|---|---|---|---|---|---|---|
| 01 | MeOH | 25° C. | 21 hr | Slurry | Gel-like substance | N/A |
| 02 | EtOH | 25° C. | 21 hr | Evaporation | Sticky liquids | N/A |
| 03 | 2-Propanol | 25° C. | 21 hr | Evaporation | Sticky liquids | N/A |
| 04 | THF | 25° C. | 21 hr | Evaporation | Gel-like substance | N/A |
| 05 | ACN | 25° C. | 21 hr | Slurry | Suspension | Pattern C-I |
| 06 | MtBE | 25° C. | 21 hr | Evaporation | Clear liquid | N/A |
| 07 | MEK | 25° C. | 21 hr | Slurry | Clear liquid | N/A |
| 08 | $H_2O$ | 25° C. | 21 hr | Slurry | Suspension | Pattern C-II |
| 09 | EA | 25° C. | 21 hr | Slurry | Gel-like substance | N/A |
| 10 | $H_2O$ | 50° C. | 42 hr | Slurry | Suspension | Pattern C-I |
| 11 | $H_2O$ | 35° C. | 65 hr | Slurry | Suspension | Pattern C-II |
| 12 | $H_2O$ | 35° C. | 89 hr | Slurry | Suspension | Pattern C-II |

The systems in which crystals were obtained by recrystallization were Batch No. 05, in which ACN was used as a solvent; and Batch Nos. 08, 10, 11, and 12, in which $H_2O$ was used as a solvent.

Figure 23:
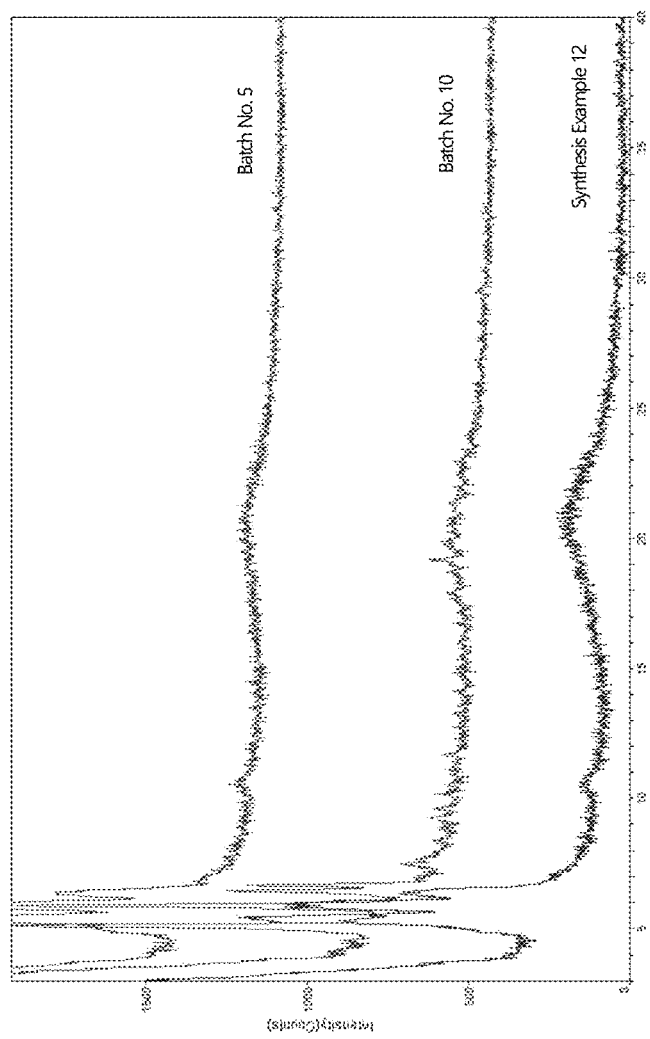
FIG. 23 shows XRPD analysis results of a solid component obtained in Batch No. 05.
Figure 24:
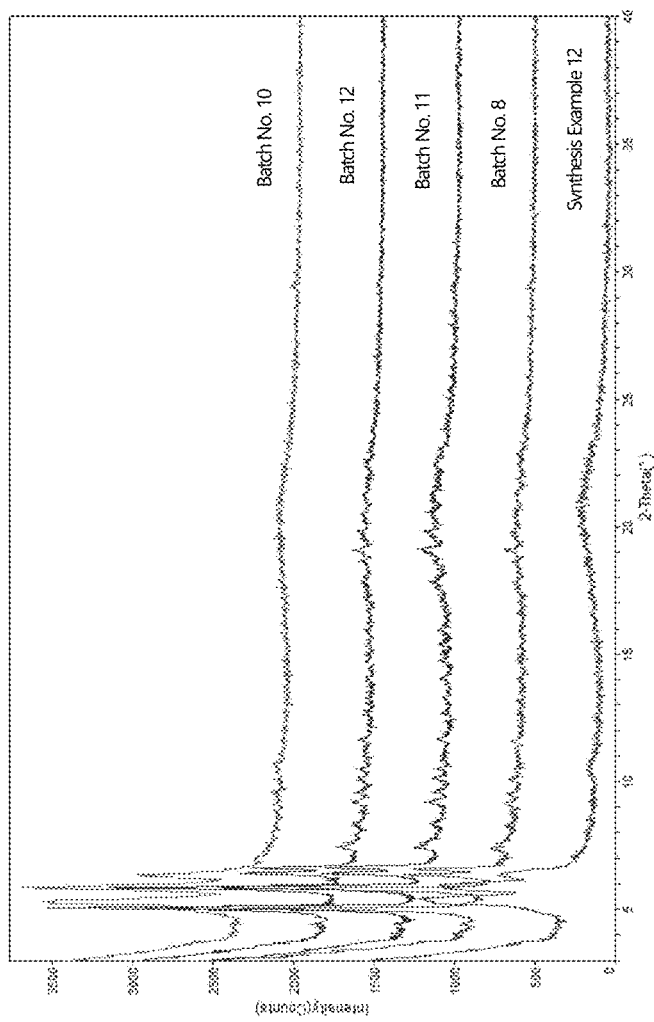
FIG. 24 shows XRPD analysis results of solid components obtained in Batch Nos. 08, 10, 11, and 12.
Figure 25:
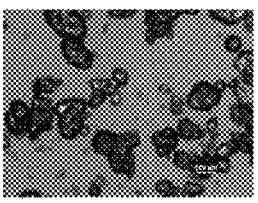
FIG. 25 shows polarizing microscopy images and XRPD analysis results of the solid components obtained in Batch Nos. 08, 10, 11, and 12.

FIGS. 23 and 24 show XRPD analysis results of the recrystallized solids. Batch Nos. 05 and 10 showed peak pattern C-I (FIG. 23). Batch Nos. 08, 11, and 12 showed pattern C-II, which is different from peak pattern C-I of Batch No. 10 and Synthesis Example 12 (FIG. 24). FIG. 25 shows polarizing microscope images of Batch Nos. 08, 10, 11, and 12.

Figures 1, 29:
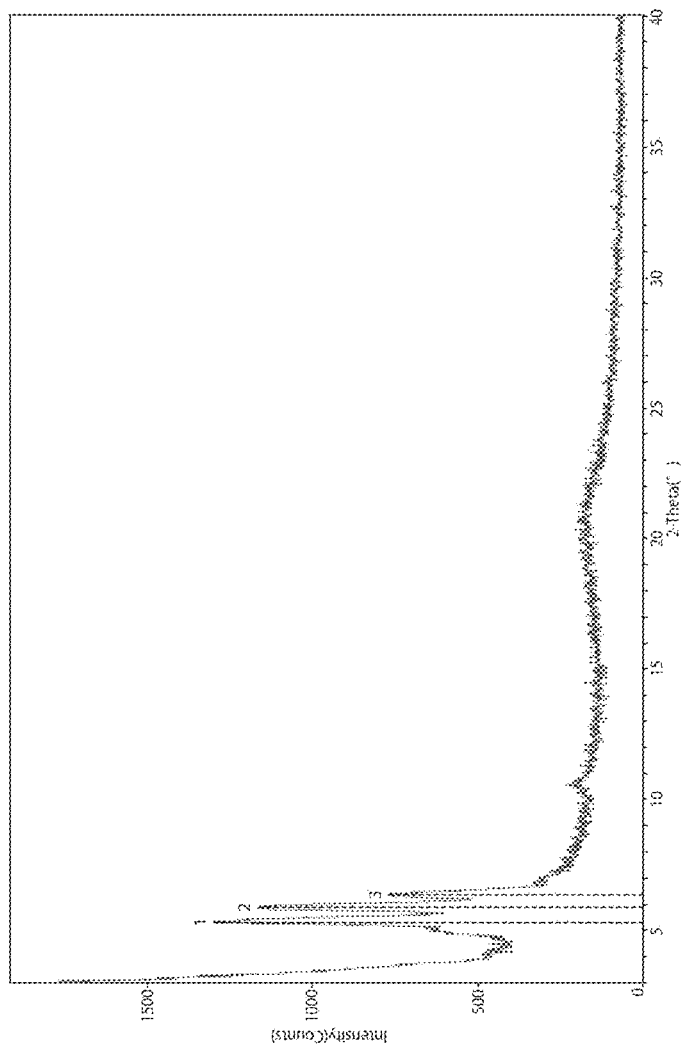
Figures 1, 30:
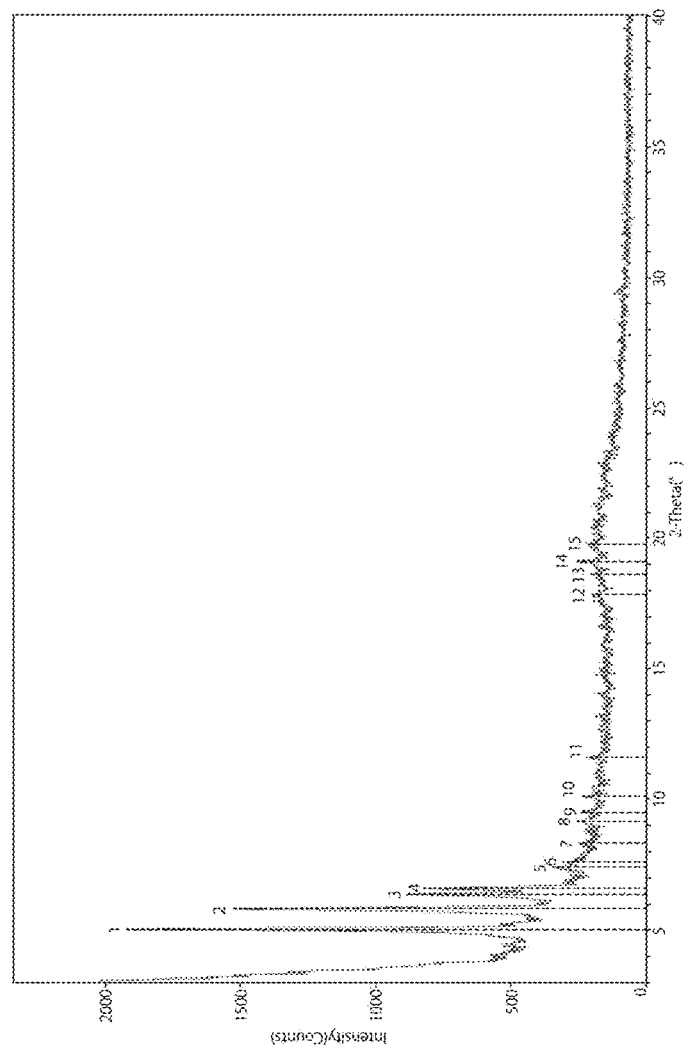
Figures 1, 31:
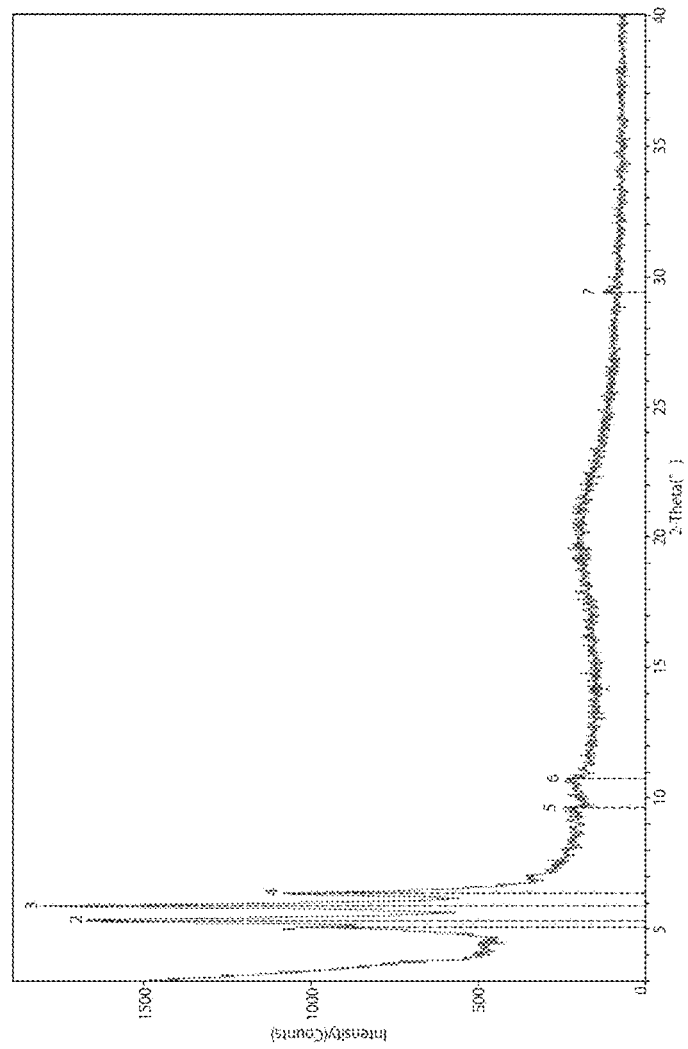
Figures 1, 32:
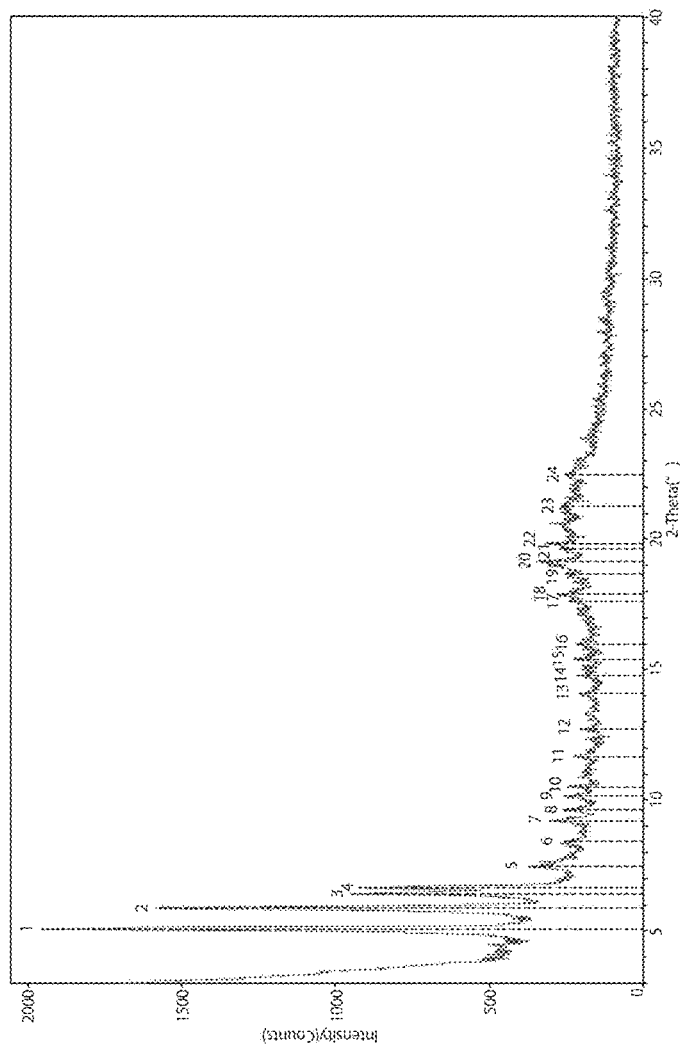
Figures 1, 33:
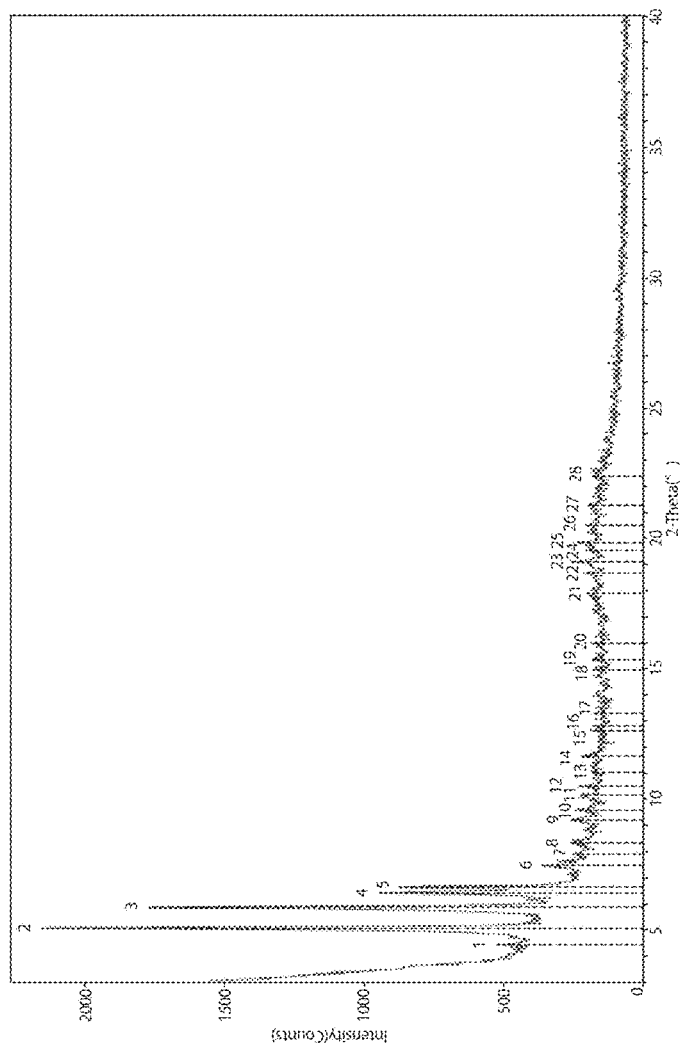

FIG. 29 shows XRPD peak values of Batch No. 05. FIG. 30 shows XRPD peak values of Batch No. 08. FIG. 31 shows XRPD peak values of Batch No. 10. FIG. 32 shows XRPD peak values of Batch No. 11. FIG. 33 shows XRPD peak values of Batch No. 12.

Further, recrystallization was attempted by the slurry method using a methanol/water mixture, an ethanol/water mixture, an ACN/water mixture, a THF/water mixture, and an EA/water mixture as solvents. However, no solid components were obtained.

Figure 26:
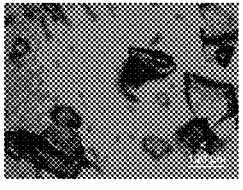
FIG. 26 shows polarizing microscopy images and XRPD analysis results of Compound of Synthesis Example 12 subjected to heat treatment.
Figure 27:
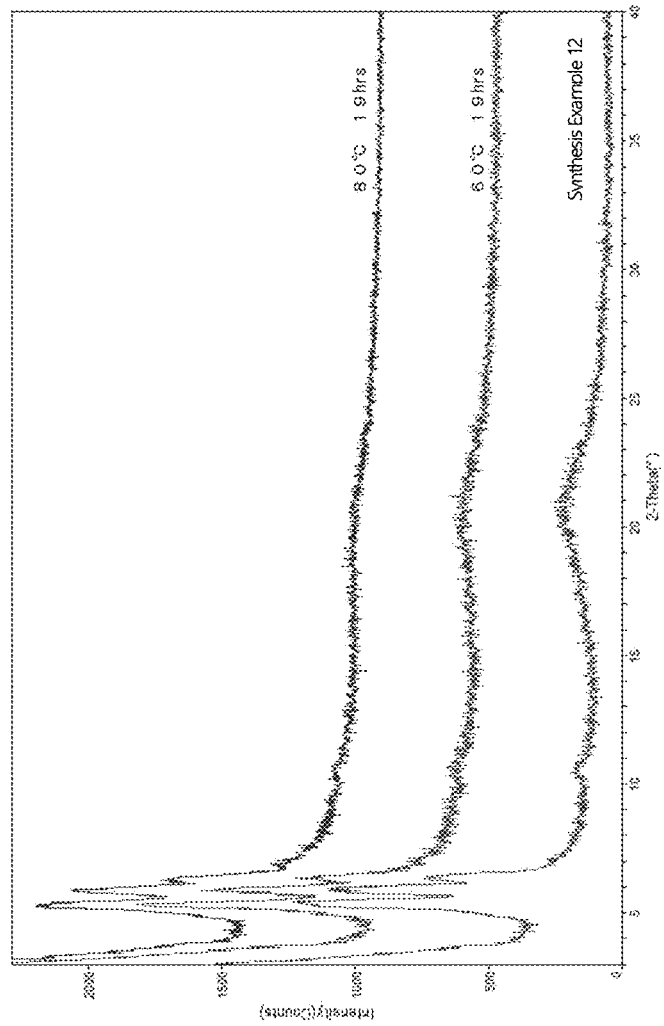
FIG. 27 shows XRPD analysis results of Compound of Synthesis Example 12 subjected to heat treatment.

9-2. Crystal Polymorph Screening by the Heating Method 30 mg of the compound of Synthesis Example 12 was placed in an open vial, and incubated in an oven heated to 60° C. or 80° C. for 19 hours or for 91 hours. After completion of the incubation, XRPD analysis and polarizing microscope observation were performed. FIG. 26 and FIG. 27 show the results. After 19 hours of the incubation, no changes in morphology or XRPD pattern were observed in the compound of Synthesis Example 12. Even after 91 hours of incubation, no morphological changes of the compound were observed.

The invention claimed is:

1. A compound represented by Formula (II) or a solvate thereof:

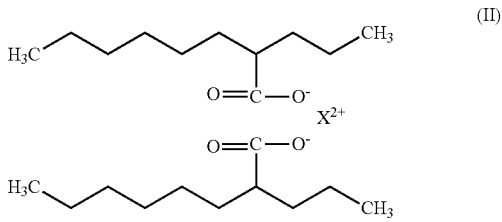

(II)

wherein $X^{2+}$ is a divalent cation, and wherein the compound has a crystal structure.

2. The compound according to claim 1, wherein $X^{2+}$ is $Ca^{2+}$.

3. A method for producing a compound represented by Formula (II):

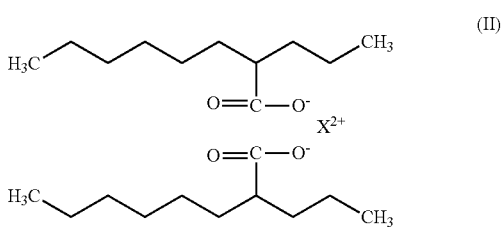

(II)

wherein $X^{2+}$ is a divalent cation, the method comprising allowing a divalent cation to act on arundic acid in at least one solvent selected from the group consisting of methyl tert-butyl ether, acetonitrile, and dichloromethane.

4. A composition comprising a combination of
(A) at least one member selected from the group consisting of compounds represented by Formula (I), pharmaceutically acceptable salts thereof, and hydrates thereof,

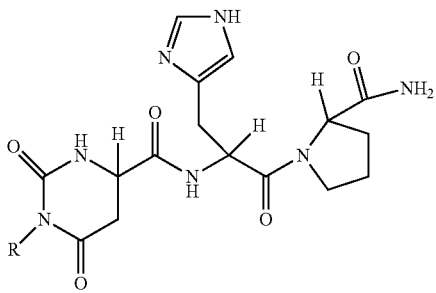

(I)

wherein R is hydrogen or $C_{1-6}$ alkyl, and (B) at least one member selected from the group consisting of the compounds according to claim 1 and solvates thereof.

5. The composition according to claim 4, which is a pharmaceutical composition.

6. The composition according to claim 4, which is a food composition.

7. A method of treating a neurodegenerative disease or cerebral infarction, the method comprising administering the composition according to claim 4 to a subject in need thereof in an effective amount to treat the neurodegenerative disease or cerebral infarction.

8. The method according to claim 7, the neurodegenerative disease is selected from dementia, Parkinson's disease, amyotrophic lateral sclerosis, Steele-Richardson-Olszewski syndrome, multiple system atrophy, and triplet repeat disease.

9. A method of ameliorating a learning disorder, the method comprising administering the composition according to claim 4 to a subject in need thereof in an amount effective to ameliorate the learning disorder.

10. The method according to claim 9, wherein the learning disorder is spatial cognitive impairment.

\* \* \* \* \*